United States Patent
Chen et al.

(10) Patent No.: US 11,339,218 B2
(45) Date of Patent: May 24, 2022

(54) HUMAN MONOCLONAL ANTIBODIES AGAINST LAG3 AND USES THEREOF

(71) Applicant: Zhejiang Shimai Pharmaceutical Co., Ltd., Hangzhou (CN)

(72) Inventors: Weizao Chen, Frederick, MD (US); Tao Fu, Frederick, MD (US); Zuoxiang Xiao, Frederick, MD (US)

(73) Assignee: Zhejiang Shimai Pharmaceutical Co., Ltd., Hangzhou (CN)

(*) Notice: Subject to any disclaimer, the term of this patent is extended or adjusted under 35 U.S.C. 154(b) by 169 days.

(21) Appl. No.: 16/611,986

(22) PCT Filed: May 9, 2018

(86) PCT No.: PCT/PC2018/031711
§ 371 (c)(1),
(2) Date: Nov. 8, 2019

(87) PCT Pub. No.: WO2018/208868
PCT Pub. Date: Nov. 15, 2018

(65) Prior Publication Data
US 2021/0115135 A1 Apr. 22, 2021

Related U.S. Application Data

(60) Provisional application No. 62/504,524, filed on May 10, 2017.

(51) Int. Cl.
*C07K 16/28* (2006.01)
*A61P 35/00* (2006.01)
(Continued)

(52) U.S. Cl.
CPC .... *C07K 16/2803* (2013.01); *A61K 39/39541* (2013.01); *A61K 2039/505* (2013.01);
(Continued)

(58) Field of Classification Search
None
See application file for complete search history.

(56) References Cited

U.S. PATENT DOCUMENTS 6,143,273 A * 11/2000 Faure ............... A61P 37/06
424/1.49
9,244,059 B2 * 1/2016 Triebel ............. A61P 37/00
(Continued)

FOREIGN PATENT DOCUMENTS

| WO | 2014008218 A1 | 1/2014 |
| WO | 2016028672 A1 | 2/2016 |
| WO | 2016040892 A1 | 3/2016 |

OTHER PUBLICATIONS

He et al., Lymphocyte-activation gene-3, an important immune checkpoint in cancer, Canc. Sci. 107:1193-1197, 2016.*
(Continued)

*Primary Examiner* — Claire Kaufman
(74) *Attorney, Agent, or Firm* — Wolf, Greenfield & Sacks, P.C.

(57) ABSTRACT

The present disclosure provides isolated monoclonal antibodies that specifically bind to LAG3 with high affinity, particularly human monoclonal antibodies. Preferably, the antibodies bind human LAG3. In certain embodiments, the antibodies bind both human and monkey LAG3 but do not bind mouse LAG3. The invention provides anti-LAG3 antibodies that can inhibit the binding of LAG3 to MHC Class II molecules and that can stimulate antigen-specific T cell responses. Nucleic acid molecules encoding the antibodies of the invention, expression vectors, host cells and methods for expressing the antibodies of the invention are also provided. Immunoconjugates, bispecific molecules and pharmaceutical compositions comprising the antibodies of the invention are also provided. This disclosure also provides methods for stimulating an immune response, as well (Continued)

as methods for treating cancer using an anti-LAG3 antibody of the invention.

21 Claims, 12 Drawing Sheets

Specification includes a Sequence Listing.

(51) Int. Cl.
    *A61K 39/395*     (2006.01)
    *A61K 39/00*     (2006.01)

(52) U.S. Cl.
    CPC ......... *A61K 2039/507* (2013.01); *A61P 35/00* (2018.01); *C07K 2317/31* (2013.01); *C07K 2317/55* (2013.01); *C07K 2317/56* (2013.01); *C07K 2317/565* (2013.01); *C07K 2317/73* (2013.01); *C07K 2317/76* (2013.01); *C07K 2317/92* (2013.01)

(56) References Cited

U.S. PATENT DOCUMENTS

2011/0150892 A1    6/2011    Thudium et al.
2016/0326248 A1    11/2016    Gutierrez et al.
2017/0101472 A1    4/2017    Ullman et al.

OTHER PUBLICATIONS

Ruffo et al., Lymphocyte-activation gene 3 (LAG3): The next immune checkpointreceptor, Sem. Immunol. 42:1011305, 2019.*
Millipore Sigma, Antibody basics. Retrieved online from: <URL:https://www.sigmaaldrich.com/US/en/technical-documents/technical-article/protein-biology/western-blotting/antibody-basics>. [Retrieved on Nov. 16, 2021], 2021.*
Richter et al., On the role of the inhibitory receptor LAG-3 in acute and chronic LCMV infection, Internat. Immunol. 22(1): 13-23, 2009.*
Graydon et al., Roles, function and relevance of LAG3 in HIV infection, PLoS Pathog. 15(1): e1007429, 14 pages, Jan. 2019.*
Nguyen, LT et al. Nature Rev. Immunology, 15 (1), 45-56, 2015.
Andrews, LP et al., Immunol. Rev. 276 (1), 80-96, 2017.
Extended European Search Report on EP18799063, dated Dec. 4, 2020.
International Search Report and Written Opinion on WO2018208868.
Woo et al., Immune Inhibitory Molecules LAG-3 and PD-1 Synergistically Regulate T-cell Function to Promote Tumoral Immune Escape, Cancer Research, 2012, vol. 72, No. 4, p. 917-927.
Shapiro et al., Lymphocyte activation gene 3: a novel therapeutic target in chronic lymphocytic leukemia, Haematologica, 2017, V102, No. 5, p. 874-882.
Zhou et al., Blockade of LAG3 enhances responses of tumor-infiltrating T cells in mismatch repair-proficient liver metastases of colorectal cancer, Oncoimminology, 2018, vol. 7, No. 7, p. 1-17.

* cited by examiner

SEQUENCE LISTING

```
<160> NUMBER OF SEQ ID NOS: 114

<210> SEQ ID NO 1
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 1

Gln Ser Val Leu Thr Gln Pro Pro Ser Val Ser Ala Ala Pro Gly Arg
1               5                   10                  15

Lys Val Thr Ile Ser Cys Ser Gly Ser Ser Ser Asn Ile Gly Thr Asn
            20                  25                  30

Ser Val Ser Trp Tyr Gln Gln Phe Pro Gly Thr Ala Pro Lys Leu Leu
        35                  40                  45

Ile Tyr Asp Asn Asn Lys Arg Leu Ser Arg Ile Pro Asp Arg Phe Ser
    50                  55                  60

Gly Ser Lys Ser Gly Thr Ser Ala Ser Leu Ala Ile Ser Gly Leu Gln
65                  70                  75                  80
```

-continued

Ser Glu Asp Glu Ala Asp Tyr Tyr Cys Ala Ala Trp Asp Asp Ser Leu
            85                  90                  95

Thr Gly Tyr Val Phe Gly Thr Gly Thr Lys Val Thr Val Leu
            100                 105                 110

<210> SEQ ID NO 2
<211> LENGTH: 107
<212> TYPE: PRT
<213> ORGANISM: Artificial Sequence
<220> FEATURE:
<223> OTHER INFORMATION: Human IgG variable domain with mutants

<400> SEQUENCE: 2

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asn Ile Gly Thr Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Ile
            85                  90                  95

Thr Phe Gly Gln Gly Thr Arg Leu Glu Ile Lys
            100                 105

<210> SEQ ID NO 3
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 3

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Ala Ile Asn
            20                  25                  30

Tyr Val Ser Trp Tyr Gln Gln Val Pro Gly Thr Val Pro Lys Leu Leu
            35                  40                  45

Ile Tyr Asp Asp Asp Lys Arg Pro Ser Gly Ile Pro Asp Arg Phe Ser
    50                  55                  60

Gly Ser Lys Ser Gly Thr Ser Ala Thr Leu Asp Ile Ser Gly Leu Gln
65                  70                  75                  80

Thr Gly Asp Glu Ala His Tyr Tyr Cys Gly Val Trp Asp Asn Ser Leu
            85                  90                  95

Leu Ala Val Leu Phe Gly Gly Gly Thr Ser Leu Thr Val Leu
            100                 105                 110

<210> SEQ ID NO 4
<211> LENGTH: 113
<212> TYPE: PRT
<213> ORGANISM: Artificial Sequence
<220> FEATURE:
<223> OTHER INFORMATION: Human IgG variable domain with mutants

<400> SEQUENCE: 4

Asp Ile Gln Leu Thr Gln Ser Pro Asp Ser Leu Ala Val Ser Leu Gly

```
            1               5                  10                 15
          Glu Arg Ala Thr Ile Asn Cys Lys Ser Ser Gln Ser Val Leu Tyr Ser
                          20                  25                  30

Ser Asn Asn Lys Asn Tyr Leu Ala Trp Tyr Gln Gln Lys Pro Gly Gln
                      35                  40                  45

Pro Pro Lys Leu Leu Ile Tyr Trp Ala Ser Thr Arg Glu Ser Gly Val
              50                  55                  60

Pro Asp Arg Phe Ser Gly Ser Gly Ser Gly Thr Asp Phe Thr Leu Thr
          65                  70                  75                  80

Ile Ser Ser Leu Gln Ala Glu Asp Val Ala Val Tyr Tyr Cys Gln Gln
                              85                  90                  95

Tyr Tyr Ser Thr Pro Phe Thr Phe Gly Pro Gly Thr Lys Val Asp Ile
                          100                 105                 110

Lys
```

<210> SEQ ID NO 5
<211> LENGTH: 107
<212> TYPE: PRT
<213> ORGANISM: Artificial Sequence
<220> FEATURE:
<223> OTHER INFORMATION: Human IgG variable domain with mutants

<400> SEQUENCE: 5

```
          Asp Ile Gln Met Thr Gln Ser Pro Ser Ser Leu Ser Ala Ser Val Gly
          1               5                  10                  15

Asp Arg Val Thr Ile Thr Cys Gln Ala Ser Gln Asp Ile Ser Asn Tyr
                          20                  25                  30

Leu Asn Trp Tyr Gln Gln Lys Pro Gly Lys Ala Pro Lys Leu Leu Ile
                      35                  40                  45

Tyr Ala Ala Ser Ile Leu Gln Ser Gly Val Pro Ser Arg Phe Ser Gly
              50                  55                  60

Ser Gly Ser Gly Thr Asp Phe Thr Leu Thr Ile Ser Ser Leu Gln Pro
          65                  70                  75                  80

Glu Asp Phe Ala Thr Tyr Tyr Cys Gln Gln Ser His Ser Tyr Ser Glu
                              85                  90                  95

Thr Phe Gly Gln Gly Thr Lys Val Glu Ile Lys
                          100                 105
```

<210> SEQ ID NO 6
<211> LENGTH: 111
<212> TYPE: PRT
<213> ORGANISM: Artificial Sequence
<220> FEATURE:
<223> OTHER INFORMATION: Human IgG variable domain with mutants

<400> SEQUENCE: 6

```
          Gln Ser Val Val Thr Gln Pro Pro Ser Val Ser Gly Ala Pro Gly Gln
          1               5                  10                  15

Arg Val Thr Val Ser Cys Thr Gly Ser Ser Ser Asn Ile Gly Ala Asp
                          20                  25                  30

Phe Asp Val His Trp Tyr Gln Gln Leu Pro Gly Thr Ala Pro Lys Leu
                      35                  40                  45

Leu Ile Tyr Gly Asn Thr Asn Arg Pro Ser Gly Val Pro Asp Arg Phe
              50                  55                  60

Ser Gly Ser Lys Ser Gly Thr Ser Ala Ser Leu Ala Ile Thr Gly Leu
          65                  70                  75                  80

Gln Ala Glu Asp Glu Ala Asp Tyr Tyr Cys Gln Ser Tyr Asp Asn Ser
```

```
                    85                  90                  95

Leu Ser Gly Val Val Phe Gly Gly Gly Thr Lys Val Thr Val Leu
            100                 105                 110

<210> SEQ ID NO 7
<211> LENGTH: 107
<212> TYPE: PRT
<213> ORGANISM: Artificial Sequence
<220> FEATURE:
<223> OTHER INFORMATION: Human IgG variable domain with mutants

<400> SEQUENCE: 7

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Ile Ser Ser Tyr
            20                  25                  30

Leu Asn Trp Tyr Gln Gln Lys Gln Gly Lys Ala Pro Gln Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 8
<211> LENGTH: 216
<212> TYPE: PRT
<213> ORGANISM: Artificial Sequence
<220> FEATURE:
<223> OTHER INFORMATION: Human IgG with mutants

<400> SEQUENCE: 8

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Ala Ile Asn
            20                  25                  30

Tyr Val Ser Trp Tyr Gln Gln Val Pro Gly Thr Val Pro Lys Leu Leu
            35                  40                  45

Ile Tyr Asp Asp Asp Lys Arg Pro Ser Gly Ile Pro Asp Arg Phe Ser
        50                  55                  60

Gly Ser Lys Ser Gly Thr Ser Ala Thr Leu Asp Ile Ser Gly Leu Gln
65                  70                  75                  80

Thr Gly Asp Glu Ala His Tyr Tyr Cys Gly Val Trp Asp Asn Ser Leu
                85                  90                  95

Leu Ala Val Leu Phe Gly Gly Gly Thr Ser Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 9
<211> LENGTH: 118
<212> TYPE: PRT
<213> ORGANISM: Artificial Sequence
<220> FEATURE:
<223> OTHER INFORMATION: Human IgG variable domain with mutants

<400> SEQUENCE: 9

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ile Thr Pro Arg Phe Asp Ala Phe Asp Ile Trp Gly Gln Gly Thr
            100                 105                 110

Met Val Thr Val Ser Ser
        115

<210> SEQ ID NO 10
<211> LENGTH: 115
<212> TYPE: PRT
<213> ORGANISM: Artificial Sequence
<220> FEATURE:
<223> OTHER INFORMATION: Human IgG variable domain with mutants

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Val Phe Asp Tyr Trp Gly Gln Gly Thr Leu Val Thr
            100                 105                 110

Val Ser Ser
        115

<210> SEQ ID NO 11
```

```
<211> LENGTH: 121
<212> TYPE: PRT
<213> ORGANISM: Artificial Sequence
<220> FEATURE:
<223> OTHER INFORMATION: Human IgG variable domain with mutants

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Trp Trp Val Asp Ala Phe Asp Ile Trp Gly
                100                 105                 110

Gln Gly Thr Met Val Thr Val Ser Ser
            115                 120

<210> SEQ ID NO 12
<211> LENGTH: 121
<212> TYPE: PRT
<213> ORGANISM: Artificial Sequence
<220> FEATURE:
<223> OTHER INFORMATION: Human IgG variable domain with mutants

<400> SEQUENCE: 12

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Lys Pro Thr Gly Tyr Tyr Gly Met Asp Val Trp Gly
                100                 105                 110

Lys Gly Thr Leu Val Thr Val Ser Ser
            115                 120

<210> SEQ ID NO 13
<211> LENGTH: 124
<212> TYPE: PRT
<213> ORGANISM: Artificial Sequence
<220> FEATURE:
<223> OTHER INFORMATION: Human IgG variable domain with mutants

<400> SEQUENCE: 13

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Pro Pro Ala Ala Tyr Tyr Tyr Tyr Gly Met Asp
            100                 105                 110

Val Trp Gly Gln Gly Thr Thr Val Thr Val Ser Ser
        115                 120

<210> SEQ ID NO 14
<211> LENGTH: 126
<212> TYPE: PRT
<213> ORGANISM: Artificial Sequence
<220> FEATURE:
<223> OTHER INFORMATION: Human IgG variable domain with mutants

<400> SEQUENCE: 14

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Gly Ala Pro Gly Tyr Tyr Tyr Asp Ser Ser Gly Tyr Tyr Ala
            100                 105                 110

Phe Asp Ile Trp Gly Gln Gly Thr Met Val Thr Val Ser Ser
        115                 120                 125

<210> SEQ ID NO 15
<211> LENGTH: 121
<212> TYPE: PRT
<213> ORGANISM: Artificial Sequence
<220> FEATURE:
<223> OTHER INFORMATION: Human IgG variable domain with mutants

<400> SEQUENCE: 15

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
            85                  90                  95

Ala Leu Asp Gly Lys Ser Gly Phe Asp Leu Ala Phe Asp Ile Trp Gly
            100                 105                 110

Gln Gly Thr Met Val Thr Val Ser Ser
            115                 120

<210> SEQ ID NO 16
<211> LENGTH: 451
<212> TYPE: PRT
<213> ORGANISM: Artificial Sequence
<220> FEATURE:
<223> OTHER INFORMATION: Human IgG with mutants

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Ser Ser Trp Trp Val Asp Ala Phe Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 17
<211> LENGTH: 448
<212> TYPE: PRT
<213> ORGANISM: Artificial Sequence
<220> FEATURE:
<223> OTHER INFORMATION: Human IgG with mutants

<400> SEQUENCE: 17

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Ser Ser Ser Trp Trp Val Asp Ala Phe Asp Ile Trp Gly
            100                 105                 110
Gln Gly Thr Met Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
```

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 18
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 18

Ser Ser Asn Ile Gly Thr Asn Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Human IgG CDR with mutants

<400> SEQUENCE: 19

Gln Asn Ile Gly Thr Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 20

Thr Ser Asn Ile Ala Ile Asn Tyr
1               5

<210> SEQ ID NO 21
<211> LENGTH: 12
<212> TYPE: PRT
<213> ORGANISM: Artificial Sequence
<220> FEATURE:
<223> OTHER INFORMATION: Human IgG CDR with mutants

<400> SEQUENCE: 21

Gln Ser Val Leu Tyr Ser Ser Asn Asn Lys Asn Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Human IgG CDR with mutants

<400> SEQUENCE: 22

Gln Asp Ile Ser Asn Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Human IgG CDR with mutants

<400> SEQUENCE: 23

Ser Ser Asn Ile Gly Ala Asp Phe Asp
1               5

<210> SEQ ID NO 24
<211> LENGTH: 6
<212> TYPE: PRT
<213> ORGANISM: Artificial Sequence
<220> FEATURE:
<223> OTHER INFORMATION: Human IgG CDR with mutants

<400> SEQUENCE: 24

Arg Arg Ile Ser Ser Tyr
1               5

<210> SEQ ID NO 25
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 25

Ala Ala Trp Asp Asp Ser Leu Thr Gly Tyr Val
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Human IgG CDR with mutants

<400> SEQUENCE: 26

Gln Gln Leu Asn Ser Tyr Pro Ile Thr

```
<210> SEQ ID NO 27
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 27

Gly Val Trp Asp Asn Ser Leu Leu Ala Val Leu
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Human IgG CDR with mutants

<400> SEQUENCE: 28

Gln Gln Tyr Tyr Ser Thr Pro Phe Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Human IgG CDR with mutants

<400> SEQUENCE: 29

Gln Gln Ser His Ser Tyr Ser Glu Thr
1               5

<210> SEQ ID NO 30
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 30

Gln Ser Tyr Asp Asn Ser Leu Ser Gly Val Val
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Human IgG CDR with mutants

<400> SEQUENCE: 31

Gln Gln Phe Asn Ser Tyr Pro Leu Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 32

Gly Gly Ser Phe Ser Gly Tyr Tyr
1               5
```

```
<210> SEQ ID NO 33
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 33

Gly Gly Thr Phe Ser Ser Tyr Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 34

Gly Tyr Thr Phe Thr Ser Tyr Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 35

Gly Gly Thr Phe Ser Ser Tyr Ala
1               5

<210> SEQ ID NO 36
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 36

Gly Gly Thr Phe Ser Ser Tyr Ala
1               5

<210> SEQ ID NO 37
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 37

Gly Tyr Ser Phe Thr Ser Tyr Trp
1               5

<210> SEQ ID NO 38
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 38

Gly Gly Thr Phe Ser Ser Tyr Ala
1               5
```

<210> SEQ ID NO 39
<211> LENGTH: 7
<212> TYPE: PRT
<213> ORGANISM: Artificial Sequence
<220> FEATURE:
<223> OTHER INFORMATION: Human IgG CDR with mutants

<400> SEQUENCE: 39

Ile Asn His Ser Gly Ser Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 40

Ile Ile Pro Ile Phe Gly Thr Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 41

Ile Ser Ala Tyr Asn Gly Asn Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 42

Ile Ile Pro Ile Phe Gly Thr Ala
1               5

<210> SEQ ID NO 43
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 43

Ile Ile Pro Ile Phe Gly Thr Ala
1               5

<210> SEQ ID NO 44
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 44

Ile Tyr Pro Gly Asp Ser Asp Thr
1               5

```
<210> SEQ ID NO 45
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 45

Ile Ile Pro Ile Phe Gly Thr Ala
1               5

<210> SEQ ID NO 46
<211> LENGTH: 12
<212> TYPE: PRT
<213> ORGANISM: Artificial Sequence
<220> FEATURE:
<223> OTHER INFORMATION: Human IgG CDR with mutants

<400> SEQUENCE: 46

Ala Arg Ile Thr Pro Arg Phe Asp Ala Phe Asp Ile
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 47

Ala Arg Asp Pro Val Phe Asp Tyr
1               5

<210> SEQ ID NO 48
<211> LENGTH: 14
<212> TYPE: PRT
<213> ORGANISM: Artificial Sequence
<220> FEATURE:
<223> OTHER INFORMATION: Human IgG CDR with mutants

<400> SEQUENCE: 48

Ala Arg Asp Ser Ser Ser Trp Trp Val Asp Ala Phe Asp Ile
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Human IgG CDR with mutants

<400> SEQUENCE: 49

Ala Arg Glu Lys Pro Thr Gly Gly Tyr Tyr Gly Met Asp Val
1               5                   10

<210> SEQ ID NO 50
<211> LENGTH: 17
<212> TYPE: PRT
<213> ORGANISM: Artificial Sequence
<220> FEATURE:
<223> OTHER INFORMATION: Human IgG CDR with mutants

<400> SEQUENCE: 50

Ala Arg Ala Ser Pro Pro Ala Ala Tyr Tyr Tyr Tyr Gly Met Asp
1               5                   10                  15

Val
```

```
<210> SEQ ID NO 51
<211> LENGTH: 19
<212> TYPE: PRT
<213> ORGANISM: Artificial Sequence
<220> FEATURE:
<223> OTHER INFORMATION: Human IgG CDR with mutants

<400> SEQUENCE: 51

Ala Ser Gly Ala Pro Gly Tyr Tyr Asp Ser Ser Gly Tyr Tyr Ala
1               5                   10                  15

Phe Asp Ile

<210> SEQ ID NO 52
<211> LENGTH: 14
<212> TYPE: PRT
<213> ORGANISM: Artificial Sequence
<220> FEATURE:
<223> OTHER INFORMATION: Human IgG CDR with mutants

<400> SEQUENCE: 52

Ala Leu Asp Gly Lys Ser Gly Phe Asp Leu Ala Phe Asp Ile
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 53

Ser Ser Asn Ile Gly Gly Asn Ser
1               5

<210> SEQ ID NO 54
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 54

Ser Ser Asn Ile Gly Arg Asn Ile
1               5

<210> SEQ ID NO 55
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 55

Ser Ser Asn Ile Gly Asn Asn Ala
1               5

<210> SEQ ID NO 56
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 56

Gly Ser Asn Leu Gln Ser Asn Thr
1               5
```

```
<210> SEQ ID NO 57
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 57

Thr Ser Asn Ile Gly Gly Asn Thr
1               5

<210> SEQ ID NO 58
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 58

Ser Ser Asn Ile Gly Ser Asn Ala
1               5

<210> SEQ ID NO 59
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 59

Arg Ser Asn Ile Gly Asn Asn Ala
1               5

<210> SEQ ID NO 60
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 60

Ser Ser Asn Ile Ala Ser Asn Ala
1               5

<210> SEQ ID NO 61
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 61

Ser Ser Asn Ile Gly Ser Asn Ile
1               5

<210> SEQ ID NO 62
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 62

Tyr Ser Asn Ile Gly Gly Asn Thr
1               5
```

```
<210> SEQ ID NO 63
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 63

Ser Ser Asn Ile Ala Ser Asn Ala
1               5

<210> SEQ ID NO 64
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 64

Ser Ser Asn Ile Gly Ser Ala Thr
1               5

<210> SEQ ID NO 65
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 65

Ser Ser Asn Ile Ala Ser Asn Ala
1               5

<210> SEQ ID NO 66
<211> LENGTH: 8
<212> TYPE: PRT
<213> ORGANISM: Artificial Sequence
<220> FEATURE:
<223> OTHER INFORMATION: Human IgG CDR with mutants

<400> SEQUENCE: 66

Ser Ser Asn Ile Gly Asn Asn Ala
1               5

<210> SEQ ID NO 67
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 67

Ala Ala Trp Asp Asp Ser Leu Asn Ala Tyr Val
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Human IgG CDR with mutants

<400> SEQUENCE: 68

Ala Ala Trp Asp Asp Ser Leu Asn Gly His Met Leu
1               5                   10
```

-continued

```
<210> SEQ ID NO 69
<211> LENGTH: 12
<212> TYPE: PRT
<213> ORGANISM: Artificial Sequence
<220> FEATURE:
<223> OTHER INFORMATION: Human IgG CDR with mutants

<400> SEQUENCE: 69

Ala Ala Trp Asp Asp Ser Leu Ser Gly Gln Val Leu
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 70

Ala Ala Trp Asp Asp Arg Leu Asp Ala Tyr Val
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 71

Ala Ala Trp Asp Asp Ser Leu Ile Ala Tyr Val
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 72

Ala Ala Trp Asp Asp Ser Leu Asn Ala Phe Val
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 73

Ala Ala Trp Asp Asp Ser Leu Asn Gly Val Leu
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 74

Ala Ala Trp Asp Asp Ser Leu Asn Gly Val Leu
1               5                   10

<210> SEQ ID NO 75
```

```
<211> LENGTH: 12
<212> TYPE: PRT
<213> ORGANISM: Artificial Sequence
<220> FEATURE:
<223> OTHER INFORMATION: Human IgG CDR with mutants

<400> SEQUENCE: 75

Ala Val Trp Asp Asp Ser Leu Asp Gly His Leu Leu
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 76

Ala Ala Trp Asp Asp Asn Leu Asn Gly Leu Val
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 77

Ala Ala Trp Asp Asp Ser Leu Asn Gly Val Leu
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 78

Ala Ala Trp Asp Gly Ser Leu Asp Gly Val Met
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 79

Ala Ala Trp Asp Asp Ser Leu Asn Gly Val Leu
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Human IgG CDR with mutants

<400> SEQUENCE: 80

Ala Ala Trp Asp Asp Ser Leu Asn Ala Val Val
1               5                   10

<210> SEQ ID NO 81
<211> LENGTH: 110
```

<212> TYPE: PRT
<213> ORGANISM: Artificial Sequence
<220> FEATURE:
<223> OTHER INFORMATION: Human IgG variable domain with mutants

<400> SEQUENCE: 81

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Ser Val Asn Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Glu Glu Ala Asp Tyr Tyr Cys Ala Ala Trp Asp Asp Ser Leu
                85                  90                  95

Asn Ala Tyr Val Phe Gly Pro Gly Thr Lys Val Thr Val Leu
            100                 105                 110

<210> SEQ ID NO 82
<211> LENGTH: 111
<212> TYPE: PRT
<213> ORGANISM: Artificial Sequence
<220> FEATURE:
<223> OTHER INFORMATION: Human IgG variable domain with mutants

<400> SEQUENCE: 82

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Ile Val Asn Trp Tyr Gln His Leu Pro Gly Thr Ala Pro Lys Leu Leu
        35                  40                  45

Ile Tyr Gly Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Met Leu Phe Gly Gly Gly Thr Lys Leu Thr Val Leu
            100                 105                 110

<210> SEQ ID NO 83
<211> LENGTH: 111
<212> TYPE: PRT
<213> ORGANISM: Artificial Sequence
<220> FEATURE:
<223> OTHER INFORMATION: Human IgG variable domain with mutants

<400> SEQUENCE: 83

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser

```
                    50                  55                  60
Gly Ser Lys Ser Gly Thr Ser Ala Ser Leu Ala Ile Ser Gly Leu Arg
 65                  70                  75                  80

Ser Glu Asp Glu Gly Asp Tyr Phe Cys Ala Ala Trp Asp Asp Ser Leu
                 85                  90                  95

Ser Gly Gln Val Leu Phe Gly Gly Gly Thr Lys Leu Thr Val Leu
            100                 105                 110

<210> SEQ ID NO 84
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 84

Ser Tyr Val Leu Thr Gln Pro Pro Ser Thr Ser Ala Ala Pro Gly Gln
  1               5                  10                  15

Thr Val Thr Ile Leu Cys Phe Gly Gly Gly Ser Asn Leu Gln Ser Asn
                 20                  25                  30

Thr Val Asn Trp Tyr Arg His Val Ser Gly Ser Ala Pro Lys Leu Leu
             35                  40                  45

Ile His Ser Asp Asp Glu Arg Ala Ser Gly Val Ser Pro Arg Leu Ser
 50                  55                  60

Gly Ser Lys Ser Gly Gly Ser Ala Ser Leu Ile Leu Arg Gly Leu Gln
 65                  70                  75                  80

Pro Glu Asp Glu Gly Asp Tyr Tyr Cys Ala Ala Trp Asp Asp Arg Leu
                 85                  90                  95

Asp Ala Tyr Val Phe Gly Thr Gly Thr Lys Val Thr Val Leu
            100                 105                 110

<210> SEQ ID NO 85
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 85

Gln Ser Val Leu Thr Gln Pro Pro Ser Ala Ser Gly Thr Pro Gly Gln
  1               5                  10                  15

Arg Val Thr Ile Ser Cys Ser Gly Ser Thr Ser Asn Ile Gly Gly Asn
                 20                  25                  30

Thr Val Asn Trp Tyr Gln Gln Leu Pro Gly Thr Ala Pro Lys Leu Leu
             35                  40                  45

Ile Tyr Ser Ser Asn Arg Arg Pro Ser Gly Val Pro Asp Arg Phe Ser
 50                  55                  60

Gly Ser Thr Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Ile Ala Tyr Val Phe Gly Thr Gly Thr Lys Val Thr Val Leu
            100                 105                 110

<210> SEQ ID NO 86
<211> LENGTH: 110
<212> TYPE: PRT
<213> ORGANISM: Artificial Sequence
<220> FEATURE:
```

<223> OTHER INFORMATION: Human IgG variable domain with mutants

<400> SEQUENCE: 86

Ser Tyr Glu Leu Thr Gln Pro Pro Ser Val Ser Glu Ala Pro Arg Gln
1               5                   10                  15

Arg Val Thr Ile Ser Cys Ser Gly Ser Ser Asn Ile Gly Ser Asn
            20                  25                  30

Ala Val Ser Trp Tyr Gln Gln Val Pro Arg Lys Ala Pro Lys Leu Leu
        35                  40                  45

Val Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Arg Gly Leu Gln
65                  70                  75                  80

Ser Glu Asp Glu Ala Asp Tyr Tyr Cys Ala Ala Trp Asp Asp Ser Leu
                85                  90                  95

Asn Ala Phe Val Phe Gly Thr Gly Thr Lys Val Thr Val Leu
            100                 105                 110

<210> SEQ ID NO 87
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 87

Ser Tyr Glu Leu Thr Gln Pro Pro Ser Val Ser Glu Ala Pro Arg Gln
1               5                   10                  15

Arg Ala Thr Ile Ser Cys Ser Gly Ser Arg Ser Asn Ile Gly Asn Asn
            20                  25                  30

Ala Val Ser Trp Tyr Gln Arg Leu Pro Gly Gln Ala Pro Lys Leu Leu
        35                  40                  45

Ile Tyr Tyr Asp Thr Phe Leu Pro Ser Gly Val Ser Asp Arg Phe Ser
    50                  55                  60

Gly Ser Lys Ser Gly Thr Ser Ala Ser Leu Thr Ile Ser Gly Leu Gln
65                  70                  75                  80

Ser Asp Asp Glu Ala Asp Tyr Tyr Cys Ala Ala Trp Asp Asp Ser Leu
                85                  90                  95

Asn Gly Val Leu Phe Gly Gly Gly Thr Lys Leu Thr Val Gln
            100                 105                 110

<210> SEQ ID NO 88
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 88

Leu Pro Val Leu Thr Gln Pro Pro Ser Val Ser Gly Ala Pro Arg Gln
1               5                   10                  15

Arg Val Thr Ile Ser Cys Ser Gly Gly Ser Ser Asn Ile Ala Ser Asn
            20                  25                  30

Ala Val Asn Trp Tyr Gln Gln Phe Pro Gly Lys Ala Pro Lys Leu Leu
        35                  40                  45

Val Tyr Tyr Asp Asp Leu Leu Pro Ser Gly Val Ser Asp Arg Phe Ser
    50                  55                  60

Gly Ser Lys Thr Gly Thr Ser Ala Ser Leu Ala Ile Ser Ala Leu Gln

```
                65                  70                  75                  80
Ser Glu Asp Glu Ala Asp Tyr Phe Cys Ala Ala Trp Asp Asp Ser Leu
                    85                  90                  95

Asn Gly Val Leu Phe Gly Gly Gly Thr Lys Leu Thr Val Leu
                100                 105                 110

<210> SEQ ID NO 89
<211> LENGTH: 111
<212> TYPE: PRT
<213> ORGANISM: Artificial Sequence
<220> FEATURE:
<223> OTHER INFORMATION: Human IgG variable domain with mutants

<400> SEQUENCE: 89

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Ile Val Asn Trp Tyr Gln His Leu Pro Gly Thr Ala Pro Lys Leu Leu
            35                  40                  45

Ile Tyr Gly Asn Ser Gln Arg Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asn Tyr Tyr Cys Ala Val Trp Asp Asp Ser Leu
                85                  90                  95

Asp Gly His Leu Leu Phe Gly Gly Gly Thr Lys Leu Thr Val Leu
                100                 105                 110

<210> SEQ ID NO 90
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 90

Ser Tyr Val Leu Thr Gln Pro Pro Ser Ala Ser Gly Thr Pro Gly Gln
1               5                   10                  15

Arg Val Thr Met Ser Cys Ser Gly Arg Tyr Ser Asn Ile Gly Gly Asn
                20                  25                  30

Thr Val Asn Trp Tyr His His Leu Pro Gly Thr Ala Pro Thr Leu Leu
            35                  40                  45

Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Val Gln
65                  70                  75                  80

Ser Glu Asp Glu Ala Asp Tyr Tyr Cys Ala Ala Trp Asp Asp Asn Leu
                85                  90                  95

Asn Gly Leu Val Phe Gly Thr Gly Thr Lys Val Thr Val Leu
                100                 105                 110

<210> SEQ ID NO 91
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 91
```

```
Pro Tyr Val Leu Thr Gln Pro Pro Ser Val Ser Gly Ala Pro Arg Gln
1               5                   10                  15

Arg Val Thr Ile Ser Cys Ser Gly Gly Ser Ser Asn Ile Ala Ser Asn
                20                  25                  30

Ala Val Asn Trp Tyr Gln Gln Phe Pro Gly Lys Ala Pro Lys Leu Leu
            35                  40                  45

Val Tyr Tyr Asp Asp Leu Leu Pro Ser Gly Val Ser Asp Arg Phe Ser
        50                  55                  60

Gly Ser Lys Thr Gly Thr Ser Ala Ser Leu Ala Ile Ser Ala Leu Gln
65                  70                  75                  80

Ser Glu Asp Glu Ala Asp Tyr Phe Cys Ala Ala Trp Asp Asp Ser Leu
                85                  90                  95

Asn Gly Val Leu Phe Gly Gly Gly Thr Lys Leu Thr Val Leu
            100                 105                 110
```

<210> SEQ ID NO 92
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 92

```
Leu Pro Val Leu Thr Gln Pro Pro Ser Ala Ser Gly Thr Pro Gly Gln
1               5                   10                  15

Arg Ile Thr Ile Ser Cys Ser Gly Ser Ser Ser Asn Ile Gly Ser Ala
                20                  25                  30

Thr Val Asn Trp Tyr Gln His Leu Pro Gly Thr Ala Pro Lys Leu Leu
            35                  40                  45

Ile Tyr Gly Asp Asn Gln Arg Pro Ser Gly Val Ala Asp Arg Phe Ser
        50                  55                  60

Gly Ser Lys Ser Gly Thr Ser Ala Ser Leu Glu Ile Arg Gly Leu Gln
65                  70                  75                  80

Ser Glu Asp Glu Ala Asp Tyr Tyr Cys Ala Ala Trp Asp Gly Ser Leu
                85                  90                  95

Asp Gly Val Met Phe Gly Gly Gly Thr Arg Val Asn Val Leu
            100                 105                 110
```

<210> SEQ ID NO 93
<211> LENGTH: 110
<212> TYPE: PRT
<213> ORGANISM: Artificial Sequence
<220> FEATURE:
<223> OTHER INFORMATION: Human IgG variable domain with mutants

<400> SEQUENCE: 93

```
Ser Tyr Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Ala Ser Asn
                20                  25                  30

Ala Val Asn Trp Tyr Gln Gln Phe Pro Gly Lys Ala Pro Lys Leu Leu
            35                  40                  45

Val Tyr Tyr Asp Asp Leu Leu Pro Ser Gly Val Ser Asp Arg Phe Ser
        50                  55                  60

Gly Ser Lys Thr Gly Thr Ser Ala Ser Leu Ala Ile Ser Ala Leu Gln
65                  70                  75                  80

Ser Glu Asp Glu Ala Asp Tyr Phe Cys Ala Ala Trp Asp Asp Ser Leu
```

```
                    85                  90                  95

Asn Gly Val Leu Phe Gly Gly Gly Thr Lys Leu Thr Val Leu
            100                 105                 110

<210> SEQ ID NO 94
<211> LENGTH: 109
<212> TYPE: PRT
<213> ORGANISM: Artificial Sequence
<220> FEATURE:
<223> OTHER INFORMATION: Human IgG variable domain with mutants

<400> SEQUENCE: 94

Ser Val Val Thr Gln Pro Pro Ser Val Ser Glu Ala Pro Arg Gln Arg
1               5                   10                  15

Val Thr Ile Ser Cys Ser Gly Ser Ser Ser Asn Ile Gly Asn Asn Ala
            20                  25                  30

Val Asn Trp Tyr Gln Gln Leu Pro Gly Lys Ala Pro Lys Leu Leu Ile
        35                  40                  45

Tyr Tyr Asp Asp Leu Leu Pro Ser Gly Val Ser Asp Arg Phe Ser Gly
    50                  55                  60

Ser Lys Ser Gly Thr Ser Ala Ser Leu Ala Ile Ser Gly Leu Gln Ser
65                  70                  75                  80

Glu Asp Glu Ala Asp Tyr Tyr Cys Ala Ala Trp Asp Asp Ser Leu Asn
                85                  90                  95

Ala Val Val Phe Gly Gly Gly Thr Lys Leu Thr Val Leu
            100                 105

<210> SEQ ID NO 95
<211> LENGTH: 46
<212> TYPE: DNA
<213> ORGANISM: Artificial Sequence
<220> FEATURE:
<223> OTHER INFORMATION: Oligo primer

<400> SEQUENCE: 95
gtgtaagctt accatgggtg tgcccactca ggtcctgggg ttgctg                46

<210> SEQ ID NO 96
<211> LENGTH: 46
<212> TYPE: DNA
<213> ORGANISM: Artificial Sequence
<220> FEATURE:
<223> OTHER INFORMATION: Oligo primer

<400> SEQUENCE: 96
gtgttctaga gccgccacca tggaatggag ctgggtcttt ctcttc                46

<210> SEQ ID NO 97
<211> LENGTH: 30
<212> TYPE: DNA
<213> ORGANISM: Artificial Sequence
<220> FEATURE:
<223> OTHER INFORMATION: Oligo primer

<400> SEQUENCE: 97
gatgccagat gtcagtctgt gttgacgcag                                  30

<210> SEQ ID NO 98
<211> LENGTH: 39
<212> TYPE: DNA
<213> ORGANISM: Artificial Sequence
<220> FEATURE:
<223> OTHER INFORMATION: Oligo primer
```

<400> SEQUENCE: 98
gccagagaat cggtcaggaa tccctgaggg tcgcttatc                              39

<210> SEQ ID NO 99
<211> LENGTH: 18
<212> TYPE: DNA
<213> ORGANISM: Artificial Sequence
<220> FEATURE:
<223> OTHER INFORMATION: Oligo primer

<400> SEQUENCE: 99
cctgaccgat tctctggc                                                    18

<210> SEQ ID NO 100
<211> LENGTH: 31
<212> TYPE: DNA
<213> ORGANISM: Artificial Sequence
<220> FEATURE:
<223> OTHER INFORMATION: Oligo primer

<400> SEQUENCE: 100
gatcgaattc ttatgaacat tctgtagggg c                                     31

<210> SEQ ID NO 101
<211> LENGTH: 30
<212> TYPE: DNA
<213> ORGANISM: Artificial Sequence
<220> FEATURE:
<223> OTHER INFORMATION: Oligo primer

<400> SEQUENCE: 101
ggtgtccact ccgaggtcca gctggtgcag                                       30

<210> SEQ ID NO 102
<211> LENGTH: 29
<212> TYPE: DNA
<213> ORGANISM: Artificial Sequence
<220> FEATURE:
<223> OTHER INFORMATION: Oligo primer

<400> SEQUENCE: 102
gaagctgagc tcacggtgac cattgtccc                                        29

<210> SEQ ID NO 103
<211> LENGTH: 32
<212> TYPE: DNA
<213> ORGANISM: Artificial Sequence
<220> FEATURE:
<223> OTHER INFORMATION: Oligo primer

<400> SEQUENCE: 103
gatcgagctc agcttccacc aagggcccat cc                                    32

<210> SEQ ID NO 104
<211> LENGTH: 36
<212> TYPE: DNA
<213> ORGANISM: Artificial Sequence
<220> FEATURE:
<223> OTHER INFORMATION: Oligo primer

<400> SEQUENCE: 104
cggccgtcgc actcatttac ccagagacag ggagag                                36

<210> SEQ ID NO 105

```
<211> LENGTH: 18
<212> TYPE: DNA
<213> ORGANISM: Artificial Sequence
<220> FEATURE:
<223> OTHER INFORMATION: Oligo primer

<400> SEQUENCE: 105
tgagtgcgac ggccggca                                                    18

<210> SEQ ID NO 106
<211> LENGTH: 18
<212> TYPE: DNA
<213> ORGANISM: Artificial Sequence
<220> FEATURE:
<223> OTHER INFORMATION: Oligo primer

<400> SEQUENCE: 106
cccgaggtcg acgctctc                                                    18

<210> SEQ ID NO 107
<211> LENGTH: 216
<212> TYPE: PRT
<213> ORGANISM: Artificial Sequence
<220> FEATURE:
<223> OTHER INFORMATION: Human IgG with mutants

<400> SEQUENCE: 107
```

Ser Tyr Glu Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Ser Asn
            20                  25                  30

Ala Val Ser Trp Tyr Gln Gln Val Pro Arg Lys Ala Pro Lys Leu Leu
        35                  40                  45

Val Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Arg Gly Leu Gln
65                  70                  75                  80

Ser Glu Asp Glu Ala Asp Tyr Tyr Cys Ala Ala Trp Asp Asp Ser Leu
                85                  90                  95

Asn Ala Phe Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

```
<210> SEQ ID NO 108
<211> LENGTH: 216
<212> TYPE: PRT
<213> ORGANISM: Artificial Sequence
```

```
<220> FEATURE:
<223> OTHER INFORMATION: Human IgG with mutants

<400> SEQUENCE: 108

Ser Tyr Val Leu Thr Gln Pro Pro Ser Ala Ser Gly Thr Pro Gly Gln
1               5                   10                  15

Arg Val Thr Met Ser Cys Ser Gly Arg Tyr Ser Asn Ile Gly Gly Asn
            20                  25                  30

Thr Val Asn Trp Tyr His His Leu Pro Gly Thr Ala Pro Thr Leu Leu
        35                  40                  45

Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Val Gln
65                  70                  75                  80

Ser Glu Asp Glu Ala Asp Tyr Tyr Cys Ala Ala Trp Asp Asp Asn Leu
                85                  90                  95

Asn Gly Leu Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Ile Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 109
<211> LENGTH: 215
<212> TYPE: PRT
<213> ORGANISM: Artificial Sequence
<220> FEATURE:
<223> OTHER INFORMATION: Human IgG with mutants

<400> SEQUENCE: 109

Ser Val Val Thr Gln Pro Pro Ser Val Ser Glu Ala Pro Arg Gln Arg
1               5                   10                  15

Val Thr Ile Ser Cys Ser Gly Ser Ser Ser Asn Ile Gly Asn Asn Ala
            20                  25                  30

Val Asn Trp Tyr Gln Gln Leu Pro Gly Lys Ala Pro Lys Leu Leu Ile
        35                  40                  45

Tyr Tyr Asp Asp Leu Leu Pro Ser Gly Val Ser Asp Arg Phe Ser Gly
    50                  55                  60

Ser Lys Ser Gly Thr Ser Ala Ser Leu Ala Ile Ser Gly Leu Gln Ser
65                  70                  75                  80

Glu Asp Glu Ala Asp Tyr Tyr Cys Ala Ala Trp Asp Asp Ser Leu Asn
                85                  90                  95

Ala Val Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
```

```
                115                 120                 125
Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 110
<211> LENGTH: 30
<212> TYPE: DNA
<213> ORGANISM: Artificial Sequence
<220> FEATURE:
<223> OTHER INFORMATION: Oligo primer

<400> SEQUENCE: 110
gatgccagat gttcctatga gctgactcag                                        30

<210> SEQ ID NO 111
<211> LENGTH: 31
<212> TYPE: DNA
<213> ORGANISM: Artificial Sequence
<220> FEATURE:
<223> OTHER INFORMATION: Oligo primer

<400> SEQUENCE: 111
gatcgaattc ttatgaacat tctgtagggg c                                      31

<210> SEQ ID NO 112
<211> LENGTH: 30
<212> TYPE: DNA
<213> ORGANISM: Artificial Sequence
<220> FEATURE:
<223> OTHER INFORMATION: Oligo primer

<400> SEQUENCE: 112
gatgccagat gttcctatgt gctgactcag                                        30

<210> SEQ ID NO 113
<211> LENGTH: 30
<212> TYPE: DNA
<213> ORGANISM: Artificial Sequence
<220> FEATURE:
<223> OTHER INFORMATION: Oligo primer

<400> SEQUENCE: 113
gatgccagat gttctgtcgt gacgcagccg                                        30

<210> SEQ ID NO 114
<211> LENGTH: 5
<212> TYPE: PRT
<213> ORGANISM: Artificial Sequence
<220> FEATURE:
<223> OTHER INFORMATION: Synthetic
```

```
<400> SEQUENCE: 114

Pro Val Gly Val Val
1               5
```

HUMAN MONOCLONAL ANTIBODIES AGAINST LAG3 AND USES THEREOF

CROSS REFERENCE TO RELATED APPLICATIONS

This application claims the benefit of U.S. Provisional Application No. 62/504,524, filed May 10, 2017, the contents of the aforementioned applications are hereby incorporated by reference in their entirety.

SEQUENCE LISTING

This application hereby incorporates by reference the material of the electronic Sequence Listing filed concurrently herewith. The material in the electronic Sequence Listing is submitted as a text (.txt) file entitled "L047370038US01-SUBSEQ-DFC" created on Dec. 27, 2021, which has a file size of 62,731 bytes, and is herein incorporated by reference in its entirety.

BACKGROUND OF THE INVENTION

LAG3 is an immune checkpoint molecule expressed on activated T and NK, and some B and DC cells. Interaction of LAG3 with its ligand, the major histocompatibility complex (MHC) class II (MHCII) expressed on antigen presenting cells like macrophages and DC, inhibits the activation of T and NK cells and therefore, suppress the ability of the cells to recognize and kill cancer cells. The present invention provides fully human monoclonal antibodies that bind to LAG3 and inhibit the interaction of LAG3 with MHCII, and therefore are able to unleash an immune system attack on cancer cells.

Antibodies targeting the immune checkpoint molecules CTLA-4 and PD1 have been approved by the US FDA to treat various tumors. However, the antibodies are effective only in some tumors and in a small population of patients with the same tumor. In addition, severe side effects are observed in some patients receiving the antibodies. LAG3 was recently discovered as a member of immune checkpoint molecules. Due to its unique dual-act functions in immune regulation, antibodies targeting LAG3, when used alone or in combination with other cancer drugs, might be more effective than the approved same class of antibodies.

In vitro studies of antigen-specific T cell responses, the addition of anti-LAG3 antibodies led to increased T cell proliferation, higher expression of activation antigens such as CD25, and higher concentrations of cytokines such as interferon-gamma and interleukin-4, supporting a role for the LAG-/MHC class II interaction in down-regulating antigen-dependent stimulation of CD4+T lymphocytes (Huard et al. (1994) Eur. J. Immunol. 24:3216-3221). Studies using a soluble LAG3 immunoglobulin fusion protein (sLAG3Ig) demonstrated direct and specific binding of LAG3 to MHC class II on the cell surface (Huard et al. (1996) Eur. J. Immunol. 26: 1180-1186). The intra-cytoplasmic region of LAG3 has been demonstrated to interact with a protein termed LAP, which is thought to be a signal transduction molecule involved in the downregulation of the CD3/TCR activation pathway (Iouzalen et al. (2001) Eur. J. Immunol. 31:2885-2891). Furthermore, CD4+CD25+ regulatory T cells (Treg) have been shown to express LAG3 upon activation and antibodies to LAG3 inhibit suppression by induced T reg cells, both in vitro and in vivo, suggesting that LAG3 contributes to the suppressor activity of Treg cells (Huang, C. et al. (2004) Immunity 21:503-513). Still further, LAG3 has been shown to negatively regulate T cell homeostasis by regulatory T cells in both T cell-dependent and independent mechanisms (Workman, C. J. and Vignali, D. A. (2005) J. Immunol. 174:688-695). In certain circumstances, LAG3 also has been shown to have immunostimulatory effects. For example, LAG3 transfected tumor cells transplanted into syngeneic mice showed marked growth reduction or complete regression as compared to untransfected tumor cells, suggesting that LAG3 expression on the tumor cells stimulated an antitumor response by triggering antigen presenting cells via MHC class II molecules (Prigent et al. (1999) Eur. J. Immunol. 29:3867-3876).

There exists a need in the art for antigen binding proteins, particularly human or humanised antibodies, that bind LAG3 and cause depletion of LAG3+ activated T cells, and which may have application in the treatment of cancer.

SUMMARY OF THE INVENTION

The present disclosure provides isolated monoclonal antibodies, in particular human monoclonal antibodies, that specifically bind LAG3 and that have desirable functional properties. These properties include high-affinity binding to human LAG3, the ability to inhibit binding of LAG3 to major histocompatibility (MHC) Class II molecules and under certain circumstances the ability to stimulate antigen-specific T cell responses. The antibodies of the invention can be used, for example, to detect LAG3 protein or to stimulate antigen-specific T cell responses, such as in a tumor-bearing subject or a virus bearing subject. In one aspect, the invention pertains to an isolated human monoclonal antibody, or an antigen-binding portion thereof, wherein the antibody binds human LAG3, inhibits binding of LAG3 to major histocompatibility (MHC) class II molecules and stimulates an immune response.

In a preferred embodiment, the antibody stimulates an antigen-specific T cell response, such as interleukin-2 (IL-2) production in an antigen-specific T cell response. In other embodiments, the antibody stimulates an immune response such as an anti-tumor response (e.g., inhibits tumor growth in an in vivo tumor graft model). In another preferred embodiment, the antibody binds an epitope of human LAG3. In still other embodiments, the antibody binds to human LAG3 with a $EC_{50}$ of $1\times10^{-6}$ M or less, or binds to human LAG3 with a $EC_{50}$ of $1\times10^{-7}$ M or less, or binds to human LAG3 with a $EC_{50}$ of $1\times10^{-8}$ M or less, or binds to human LAG3 with a $EC_{50}$ of $1\times10^{-9}$ M or less as measured by ELISA against human LAG3. In one embodiment, the antibody stains pituitary tissue by immunohistochemistry, whereas in another embodiment, the antibody does not stain pituitary tissue by immunohistochemistry.

In another aspect, the invention pertains to an isolated human monoclonal antibody, or antigen-binding portion thereof comprises:

(a) a heavy chain variable region comprising the amino acid sequence of SEQ ID NO:9 and a light chain variable region comprising the amino acid sequence of SEQ ID NO:1; or (b) a heavy chain variable region comprising the amino acid sequence of SEQ ID NO:10 and a light chain variable region comprising the amino acid sequence of SEQ ID NO:2; or (c) a heavy chain variable region comprising the amino acid sequence of SEQ ID NO:11 and a light chain variable region comprising the amino acid sequence of SEQ ID NO:3, 81-94; or (d) a heavy chain variable region comprising the amino acid sequence of SEQ ID NO:12 and a light chain variable region comprising the amino acid sequence of SEQ ID NO:4; or (e) a heavy chain variable region comprising the amino acid sequence of SEQ ID NO:13 and a light chain variable region comprising the amino acid sequence of SEQ ID NO:5; or (f) a heavy chain variable region comprising the amino acid sequence of SEQ ID NO:14 and a light chain variable region comprising the amino acid sequence of SEQ ID NO:6; or (g) a heavy chain variable region comprising the amino acid sequence of SEQ ID NO:15 and a light chain variable region comprising the amino acid sequence of SEQ ID NO:7.

In a preferred embodiment, the reference antibody comprises a heavy chain variable region consisting the amino acid sequence of SEQ ID NO:9 and a light chain variable region consisting the amino acid sequence of SEQ ID NO:1. In another preferred embodiment, the reference antibody comprises a heavy chain variable region consisting the amino acid sequence of SEQ ID NO:10 and a light chain variable region consisting the amino acid sequence of SEQ ID NO:2. In another preferred embodiment, the reference antibody comprises a heavy chain variable region consisting the amino acid sequence of SEQ ID NO:11 and a light chain variable region consisting the amino acid sequence of SEQ ID NO:3, 81-94. In another preferred embodiment, the reference antibody comprises a heavy chain variable region consisting the amino acid sequence of SEQ ID NO:12 and a light chain variable region consisting the amino acid sequence of SEQ ID NO:4. In another preferred embodiment, the reference antibody comprises a heavy chain variable region consisting the amino acid sequence of SEQ ID NO:13 and a light chain variable region consisting the amino acid sequence of SEQ ID NO:5. In another preferred embodiment, the reference antibody comprises a heavy chain variable region consisting the amino acid sequence of SEQ ID NO:14 and a light chain variable region consisting the amino acid sequence of SEQ ID NO:6. In another preferred embodiment, the reference antibody comprises a heavy chain variable region consisting the amino acid sequence of SEQ ID NO:15 and a light chain variable region consisting the amino acid sequence of SEQ ID NO:7.

In another aspect, the invention pertains to an isolated monoclonal antibody, or an antigen-binding portion thereof, comprising a heavy chain variable region that is the product of or derived from a human VH4-34 gene, a human VH 1-69 gene, a human VH1-18 gene, or a human VH5-51 gene, wherein the antibody specifically binds human LAG3.

In another aspect, the invention pertains to an isolated monoclonal antibody, or an antigen-binding portion thereof, comprising a light chain variable region that is the product of or derived from a human VL1-51 gene, a human V K1-39 gene, a human V K4-1 gene, a human VL1-40 gene or a human VK1-39 gene, wherein the antibody specifically binds human LAG3. In a preferred embodiment, the invention provides an isolated monoclonal antibody, or an antigen-binding portion thereof, comprising:

(a) a heavy chain variable region that is the product of or derived from a human VH4-34 gene and a light chain variable region that is the product of or derived from a human VL1-51 gene;

(b) a heavy chain variable region that is the product of or derived from a human VH 1-69 gene and a light chain variable region that is the product of or derived from a human VK1-39 gene;

(c) a heavy chain variable region that is the product of or derived from a human VH 1-18 gene and a light chain variable region that is the product of or derived from a human VL1-51 gene;

(d) a heavy chain variable region that is the product of or derived from a human VH 1-69 gene and a light chain variable region that is the product of or derived from a human VK 4-1 gene; or (e) a heavy chain variable region that is the product of or derived from a human VH 5-51 gene and a light chain variable region that is the product of or derived from a human VL1-40 gene;

(f) a heavy chain variable region that is the product of or derived from a human VH1-69 gene and a light chain variable region that is the product of or derived from a human VK1-9 gene;

wherein the antibody specifically binds human LAG3.

The antibodies of the invention can be, for example, full-length antibodies, for example of an IgG1, IgG2, IgG3 or IgG4 isotype. In a preferred embodiment, the antibody is an IgG4 isotype. In another preferred embodiment, the antibody is an IgG4 isotype having a serine to proline mutation in the heavy chain constant region hinge region (at a position corresponding to position 241 as described in Angal et al. (1993) Mol. Immunol. 30:105-108), such that inter-heavy chain disulfide bridge heterogeneity is reduced or abolished. Alternatively, the antibodies can be antibody fragments, such as Fab, Fab' F(ab')2 fragment, diabody, triabody, tetrabody, single-chain variable region fragment (scFv), disulfide-stabilized variable region fragment (dsFv) and half antibodies.

Accordingly, in another aspect, this disclosure provides an isolated monoclonal IgG4 antibody, or antigen-binding portion thereof, comprising:

(a) a heavy chain comprising the amino acid sequence of SEQ ID NO:17 and (b) a light chain comprising the amino acid sequence of SEQ ID NO:107, SEQ ID NO:108 or SEQ ID NO:109; wherein the antibody binds human LAG3, inhibits binding of LAG3 to major histocompatibility (MHC) class II molecule and stimulates an immune response.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:20; (e) a light chain variable region CDR2 comprising DDD; and (f) a light chain variable region CDR3 comprising SEQ ID NO:27; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:53; (e) a light chain variable region CDR2 comprising SDN; and (f) a light chain variable region CDR3 comprising SEQ ID NO:67; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:54; (e) a light chain variable region CDR2 comprising GNS; and (f) a light chain variable region CDR3 comprising SEQ ID NO:68; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:55; (e) a light chain variable region CDR2 comprising YDD; and (f) a light chain variable region CDR3 comprising SEQ ID NO:69; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:56; (e) a light chain variable region CDR2 comprising SDD; and (f) a light chain variable region CDR3 comprising SEQ ID NO:70; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:57; (e) a light chain variable region CDR2 comprising SSN; and (f) a light chain variable region CDR3 comprising SEQ ID NO:71; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:58; (e) a light chain variable region CDR2 comprising YDD; and (f) a light chain variable region CDR3 comprising SEQ ID NO:72; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:59; (e) a light chain variable region CDR2 comprising YDT; and (f) a light chain variable region CDR3 comprising SEQ ID NO:73; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:60; (e) a light chain variable region CDR2 comprising YDD; and (f) a light chain variable region CDR3 comprising SEQ ID NO:74; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:61; (e) a light chain variable region CDR2 comprising GNS; and (f) a light chain variable region CDR3 comprising SEQ ID NO:75; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:62; (e) a light chain variable region CDR2 comprising SND; and (f) a light chain variable region CDR3 comprising SEQ ID NO:76; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:63; (e) a light chain variable region CDR2 comprising YDD; and (f) a light chain variable region CDR3 comprising SEQ ID NO:77; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:64; (e) a light chain variable region CDR2 comprising GDN; and (f) a light chain variable region CDR3 comprising SEQ ID NO:78; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:65; (e) a light chain variable region CDR2 comprising YDD; and (f) a light chain variable region CDR3 comprising SEQ ID NO:79; wherein the antibody competes for MHC-II receptor binding to human LAG3.

Accordingly, in another aspect, this disclosure provides an isolated monoclonal antibody, or antigen-binding portion thereof comprising: (a) a heavy chain variable region CDR1 comprising SEQ ID NO:34; (b) a heavy chain variable region CDR2 comprising SEQ ID NO:41; (c) a heavy chain variable region CDR3 comprising SEQ ID NO:48; (d) a light chain variable region CDR1 comprising SEQ ID NO:66; (e) a light chain variable region CDR2 comprising YDD; and (f) a light chain variable region CDR3 comprising SEQ ID NO:80; wherein the antibody competes for MHC-II receptor binding to human LAG3.

Compositions comprising an antibody, or antigen-binding portion thereof, or immunoconjugate or bispecific molecule of the invention and a pharmaceutically acceptable carrier are also provided.

In another aspect, the invention pertains to methods of stimulating immune responses using the anti-LAG3 antibodies of the invention. For example, in one embodiment, the invention provides a method of stimulating an antigen-specific T cell response comprising contacting said T cell with an antibody of the invention such that an antigen-specific T cell response is stimulated. In a preferred embodiment, interleukin-2 production by the antigen-specific T cell is stimulated.

In another embodiment, the invention provides a method of stimulating an immune response (e.g., an antigen-specific T cell response) in a subject comprising administering an antibody of the invention to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In yet another aspect, the invention provides a method for inhibiting growth of tumor cells in a subject comprising administering to the subject an antibody of the invention such that growth of the tumor is inhibited in the subject. In still another aspect, the invention provides a method for treating viral infection in a subject comprising administering to the subject an antibody of the invention such that the viral infection is treated in the subject.

In yet another aspect, the invention provides a method for stimulating an immune response in a subject comprising administering to the subject an anti-LAG3 antibody and at least one additional immunostimulatory antibody including but not limited to an anti-PD-1 antibody, an anti-PD-L1 antibody and an anti-CTLA-4 antibody, such that an immune response is stimulated in the subject, for example to inhibit tumor growth or to stimulate an anti-viral response. In one embodiment, the subject is administered an anti-LAG3 antibody and an anti-PD-1 antibody. In another embodiment, the subject is administered an anti-LAG3 antibody and an anti-PD-L1 antibody. In yet another embodiment, the subject is administered an anti-LAG3 antibody and an anti-CTLA-4 antibody. In one embodiment, the anti-LAG3 antibody is a human antibody, such as an antibody of the disclosure. Alternatively, the anti-LAG3 antibody can be, for example, a chimeric or humanized antibody. In another embodiment, the at least one additional immunostimulatory antibody (e.g., anti-PD-1, anti-PD-L1 and/or anti-CTLA-4 antibody) is a human antibody. Alternatively, the at least one additional immunostimulatory antibody can be, for example, a chimeric or humanized antibody.

In yet another aspect, the invention pertains to a method for preparing an anti-LAG3 antibody. The method comprises:

(a) providing a heavy chain variable region antibody sequence selected from the group consisting of SEQ ID NOs:9-15, and a light chain variable region antibody sequence selected from the group consisting of SEQ ID NOs:1-7;

(b) altering at least one amino acid residue within the heavy chain variable region antibody sequence or the light chain variable region antibody sequence to create at least one altered antibody sequence; and (c) expressing the altered antibody sequence as a protein.

Other features and advantages of the instant disclosure will be apparent from the following detailed description and examples, which should not be construed as limiting. The contents of all references, GenBank entries, patents and published patent applications cited throughout this application are expressly incorporated herein by reference.

DETAILED DESCRIPTION OF THE INVENTION

Figure 1:
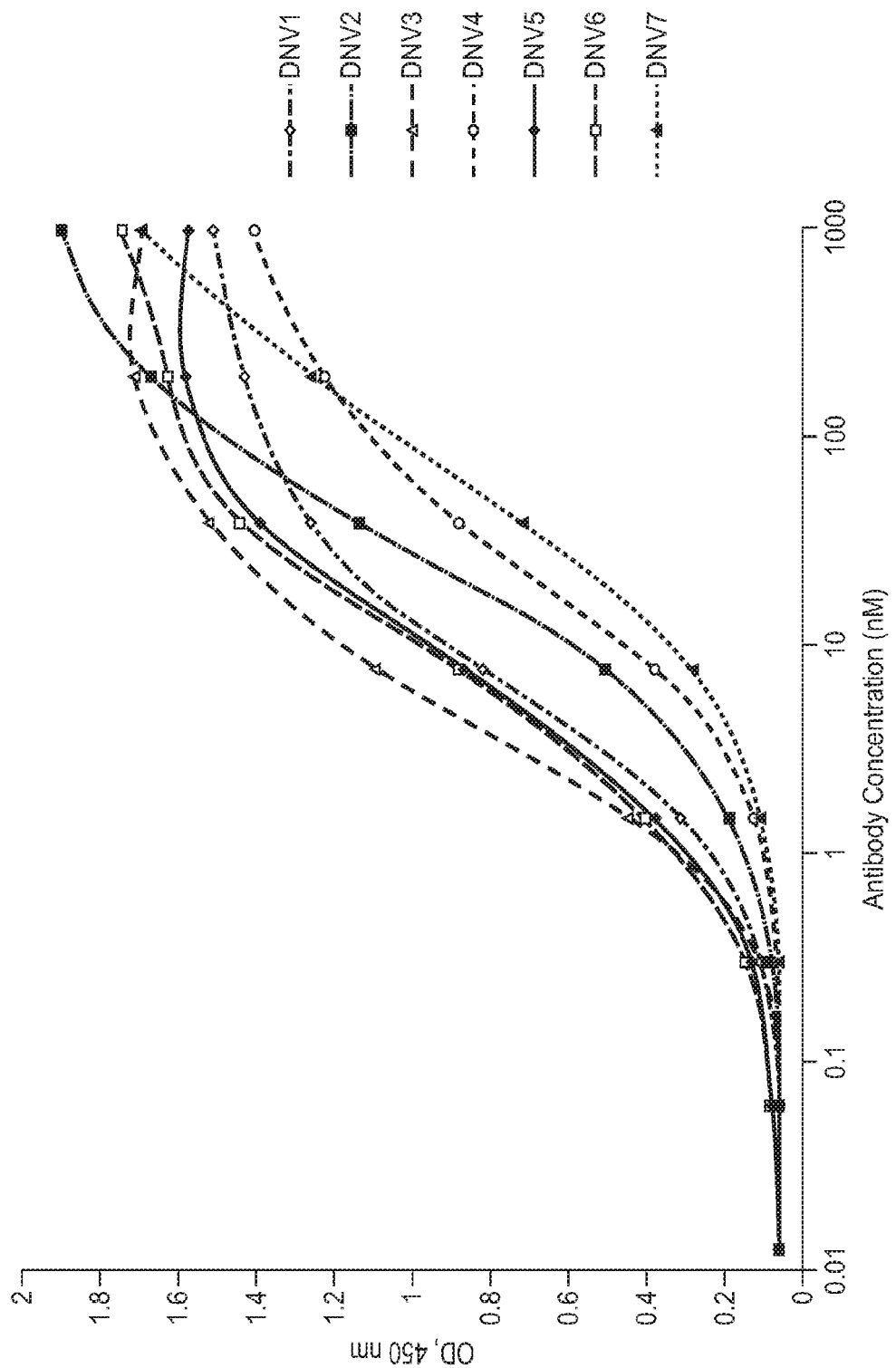
FIG. 1 illustrates binding of antibodies in the format of antigen-binding fragments (Fab) to recombinant human LAG3 as measured by enzyme-linked immunosorbent assay (ELISA).

The present disclosure relates to isolated monoclonal antibodies, particularly human monoclonal antibodies, which bind to human LAG3 and that have desirable functional properties. In certain embodiments, the antibodies of the invention are derived from particular heavy and light chain germline sequences and/or comprise particular structural features such as CDR regions comprising particular amino acid sequences. This disclosure provides isolated antibodies, methods of making such antibodies, immunoconjugates and bispecific molecules comprising such antibodies and pharmaceutical compositions containing the antibodies, immunoconjugates or bispecific molecules of the invention. This disclosure also relates to methods of using the antibodies, such as to detect LAG3 protein, as well as to methods of using the anti-LAG3 antibodies of the invention to stimulate immune responses, alone or in combination with other immunostimulatory antibodies. Accordingly, this disclosure also provides methods of using the anti-LAG3 antibodies of the invention to, for example, inhibit tumor growth or treat viral infection.

Definition

In order that the present disclosure may be more readily understood, certain terms are first defined. Additional definitions are set forth throughout the detailed description.

The term "LAG3" refers to Lymphocyte Activation Gene-3. The term "LAG3" includes variants, isoforms, homologs, orthologs and paralogs. For example, antibodies specific for a human LAG3 protein may, in certain cases, cross-react with a LAG3 protein from a species other than human. In other embodiments, the antibodies specific for a human LAG3 protein may be completely specific for the human LAG3 protein and may not exhibit species or other types of cross-reactivity, or may cross-react with LAG3 from certain other species but not all other species (e.g., cross-react with monkey LAG3 but not mouse LAG3). The term "human LAG3" refers to human sequence LAG3, such as the complete amino acid sequence of human LAG3 having GenBank Accession No. NP_002277. The term "mouse LAG3" refers to mouse sequence LAG3, such as the complete amino acid sequence of mouse LAG3 having GenBank Accession No. NP_032505. LAG3 is also known in the art as, for example, CD223. The human LAG3 sequence may differ from human LAG3 of GenBank Accession No. NP_002277 by having, e.g., conserved mutations or mutations in non-conserved regions and the LAG3 has substantially the same biological function as the human LAG3 of GenBank Accession No. NP_002277. For example, a biological function of human LAG3 is having an epitope in the extracellular domain of LAG3 that is specifically bound by an antibody of the instant disclosure or a biological function of human LAG3 is binding to MHC Class II molecules.

A particular human LAG3 sequence will generally be at least 90% identical in amino acids sequence to human LAG3 of GenBank Accession No. NP_002277 and contains amino acid residues that identify the amino acid sequence as being human when compared to LAG3 amino acid sequences of other species (e.g., murine). In certain cases, a human LAG3 can be at least 95%, or even at least 96%, 97%, 98%, or 99% identical in amino acid sequence to LAG3 of GenBank Accession No. NP_002277. In certain embodiments, a human LAG3 sequence will display no more than 10 amino acid differences from the LAG3 sequence of GenBank Accession No. NP_002277. In certain embodiments, the human LAG3 can display no more than 5, or even no more than 4, 3, 2, or 1 amino acid difference from the LAG3 sequence of GenBank Accession No. NP_002277. Percent identity can be determined as described herein The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "antigen-specific T cell response" refers to responses by a T cell that result from stimulation of the T cell with the antigen for which the T cell is specific. Non-limiting examples of responses by a T cell upon antigen-specific stimulation include proliferation and cytokine production (e.g., IL-2 production).

The term "antibody" as referred to herein includes whole antibodies, F(ab')2 fragment, diabody, triabody, tetrabody, bispecific antibody, monomeric antibodies and any antigen binding fragment (i.e., "antigen-binding portion") or single-chain variable region fragment (scFv), or disulfide-stabilized variable region fragment (dsFv) thereof. Whole antibodies are glycoproteins comprising at least two heavy (H) chains and two light (L) chains inter-connected by disulfide bonds. Each heavy chain is comprised of a heavy chain variable region (abbreviated herein as V H) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and V L regions can be further subdivided into regions of hypervariability, termed complementarity determining regions (CDR), interspersed with regions that are more conserved, termed framework regions (FR). Each V Hand V L is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., a LAG3 protein). It has been shown that the antigen-binding function of an antibody can be performed by fragments of a full-length antibody. Examples of binding fragments encompassed within the term "antigen binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the VH and CH1 domains; (v) a Fv fragment consisting of the VL and VH domains of a single arm of an antibody, (vi) a dAb fragment (Ward et al., (1989) Nature 341:544-546), which consists of a VH domain; (vii) an isolated complementarity determining region (CDR); and (viii) a nanobody, a heavy chain variable region containing a single variable domain and two constant domains. Furthermore, although the two domains of the Fv fragment, VL and VH are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988)

Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a LAG3 protein is substantially free of antibodies that specifically bind antigens other than LAG3 proteins). An isolated antibody that specifically binds a human LAG3 protein may, however, have cross-reactivity to other antigens, such as LAG3 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The CDR regions are delineated using the Kabat system (Kabat et al. (1991) Sequences of [0134] Proteins of Immunological Interest, Fifth Edition, U.S. Department of Health and Human Services, NIH Publication No. 91-3242).

The term "human monoclonal antibody" refers to antibodies displaying a single binding specificity, which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "isotype" refers to the antibody class (e.g., IgM or IgG 1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds human LAG3" is intended to refer to an antibody that binds to human LAG3 protein (and possibly a LAG3 protein from one or more non-human species) but does not substantially bind to non-LAG3 proteins. Preferably, the antibody binds to a human LAG3 protein with "high affinity", namely with a $EC_{50}$ of $1 \times 10^{-7}$ M or less, more preferably $5 \times 10^{-8}$ M or less, more preferably $3 \times 10^{-8}$ M or less, more preferably $1 \times 10^{-8}$ M or less, more preferably $5 \times 10^{-9}$ M or less or even more preferably $1 \times 10^{-9}$ M or less.

The term "does not substantially bind" to a protein or cells, as used herein, means does not bind or does not bind with a high affinity to the protein or cells, i.e. binds to the protein or cells with an $EC_{50}$ of $2 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "high affinity" for an IgG antibody refers to an antibody having an $EC_{50}$ of $1 \times 10^{-6}$ M or less, more preferably $1 \times 10^{-7}$ M or less, even more preferably $1 \times 10^{-8}$ M or less, even more preferably $1 \times 10^{-9}$ M or less, Even more preferably $1 \times 10^{-10}$ M or less for a target antigen. However, "high affinity" binding can vary for other antibody isotypes.

The term "subject" includes any human or nonhuman animal. The term "nonhuman animal" includes all vertebrates, e.g., mammals and non-mammals, such as nonhuman primates, sheep, dogs, cats, cows, horses, chickens, amphibians, and reptiles, although mammals are preferred, such as non-human primates, sheep, dogs, cats, cows and horses.

Anti-LAG3 antibodies of the invention are characterized by particular functional features or properties of the antibodies. For example, the antibodies specifically bind to human LAG3 and may bind to LAG3 from certain other species, e.g., monkey LAG3 (e.g., cynomolgus monkey, rhesus monkey), but do not substantially bind to LAG3 from certain other species, e.g., mouse LAG3. Preferably, an antibody of the invention binds to human LAG3 with high affinity.

The ability of the antibody to stimulate an immune response, such as an antigen-specific T cell response, can be indicated by, for example, the ability of the antibody to stimulate interleukin-2 (IL-2) production in an antigen-specific T cell response. In certain embodiments, an antibody of the invention binds to human LAG3 and exhibits an ability to stimulate an antigen-specific T cell response. In other embodiments, an antibody of the invention binds to human LAG3 but does not exhibit an ability to stimulate an antigen-specific T cell response. Other means by which to evaluate the ability of the antibody to stimulate an immune response include the ability of the antibody to inhibit tumor growth, such as in an in vivo tumor graft model.

The binding of an antibody of the invention to LAG3 can be assessed using one or more techniques well established in the art. For example, in a preferred embodiment, an antibody can be tested by ELISA assays, for example using a recombinant LAG3 protein (see, e.g., Example 1 for a suitable assay). Still other suitable binding assays include a flow cytometry assay in which the antibody is reacted with a cell line that expresses human LAG3, such as CHO cells that have been transfected to express LAG3 (e.g., human LAG3) on their cell surface. Other suitable cells for use in flow cytometry assays include PHA-Activated Human PBMCs and anti-CD3-stimulated CD4+ activated T cells, which express native LAG3. LAG3-Negative B Lymphoma Cell Line BJAB can be used as negative control for flow cytometry assay for LAG3. Additionally or alternatively, the binding of the antibody, including the binding kinetics (e.g., $K_D$ value) can be tested in BIAcore binding assays.

Preferably, an antibody of the invention binds to a LAG3 protein with an $EC_{50}$ of $5\times10^{-8}$ M or less, binds to a LAG3 protein with an $EC_{50}$ of $2\times10^{-8}$ M or less, binds to a LAG3 protein with an $EC_{50}$ of $5\times10^{-9}$ M or less, binds to a LAG3 protein with an $EC_{50}$ of $4\times10^{-9}$ M or less, binds to a LAG3 protein with an $EC_{50}$ of $3\times10^{-9}$ M or less, binds to a LAG3 protein with an $EC_{50}$ of $2\times10^{-9}$ M or less, binds to a LAG3 protein with an $EC_{50}$ of $1\times10^{-9}$ M or less.

Typically, an antibody of the invention binds to LAG3 in lymphoid tissues, such as tonsil, spleen or thymus, which can be detected by immunohistochemistry. Additionally, as described further in Example 8, certain anti-LAG3 antibodies of the invention stain pituitary tissue (e.g., are retained in the pituitary) as measured by immunohistochemistry, whereas other anti-LAG3 antibodies of the invention do not stain pituitary tissue (e.g., are not retained in the pituitary) as measured by immunohistochemistry. Thus, in one embodiment, the invention provides a human anti-LAG3 antibody that stains pituitary tissue by immunohistochemistry, whereas in another embodiment, the invention provides a human anti-LAG3 antibody that does not stain pituitary tissue by immunohistochemistry.

Preferred antibodies of the invention are human monoclonal antibodies. Additionally or alternatively, the antibodies can be, for example, antigen-binding portion thereof, bispecific or monomeric monoclonal antibodies.

Preferred antibodies of the invention are the human monoclonal antibodies. Fab portion of DNV1, DNV2, DNV3, DNV4, DNV5, DNV6 or DNV7 are isolated and structurally characterized as described in Example 1. The VL amino acid sequences of DNV1, DNV2, DNV3, DNV4, DNV5, DNV6 or DNV7 are shown in SEQ ID NOs:1-7, respectively. The VH amino acid sequences of DNV1, DNV2, DNV3, DNV4, DNV5, DNV6 or DNV7 are shown in SEQ ID NOs:9-15, respectively. Human IgG1 and IgG4 antibodies with DNV3 VL and VH were described in Example 2. The heavy chain amino acid sequence of DNV3 IgG1 is shown in SEQ ID NO:16. The light chain amino acid sequence of DNV3 IgG1 is shown in SEQ ID NO:8. The heavy chain amino acid sequence of DNV3 IgG4 is shown in SEQ ID NO:17. The light chain amino acid sequence of DNV3 IgG4 is shown in SEQ ID NO:8. Human IgG4 antibodies of affinity-matured DNV3 variants were described in Example 4. The heavy chain amino acid sequences of DNV3.7 IgG4, DNV3.13 IgG4 or DNV3.18 IgG4 is shown in SEQ ID NO:17. The light chain amino acid sequence of DNV3.7 IgG4, DNV3.13 IgG4 or DNV3.18 IgG4 is shown in SEQ ID NO:107, SEQ ID NO:108 or SEQ ID NO:109 respectively.

Given that each of these antibody Fab can bind to human LAG3, the VH and VL sequences can be "mixed and matched" to create other anti-LAG3 binding molecules of the invention. Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence.

Accordingly, in one aspect, this disclosure provides an isolated monoclonal antibody, or antigen-binding portion thereof comprising:

(a) a heavy chain variable region comprising an amino acid sequence selected from the group consisting of SEQ ID NOs:9-16; and (b) a light chain variable region comprising an amino acid sequence selected from the group consisting of SEQ ID NOs:1-7, 81-94;

wherein the antibody specifically binds human LAG3.

Preferred heavy and light chain combinations include:

(a) a heavy chain variable region comprising the amino acid sequence of SEQ ID NO:9 and a light chain variable region comprising the amino acid sequence of SEQ ID NO:1;

(b) a heavy chain variable region comprising the amino acid sequence of SEQ ID NO:10 and a light chain variable region comprising the amino acid sequence of SEQ ID NO:2;

(c) a heavy chain variable region comprising the amino acid sequence of SEQ ID NO:11 and a light chain variable region comprising the amino acid sequence of SEQ ID NO:3, 81-94;

(d) a heavy chain variable region comprising the amino acid sequence of SEQ ID NO:12 and a light chain variable region comprising the amino acid sequence of SEQ ID NO:4;

(e) a heavy chain variable region comprising the amino acid sequence of SEQ ID NO:13 and a light chain variable region comprising the amino acid sequence of SEQ ID NO:5; or (f) a heavy chain variable region comprising the amino acid sequence of SEQ ID NO:14 and a light chain variable region comprising the amino acid sequence of SEQ ID NO:6.

(g) a heavy chain variable region comprising the amino acid sequence of SEQ ID NO:15 and a light chain variable region comprising the amino acid sequence of SEQ ID NO:7.

In another aspect, this disclosure provides antibodies that comprise the heavy chain and light chain CDR1s, CDR2s and CDR3s of DNV1, DNV2, DNV3, DNV4, DNV5, DNV6 or DNV7, or combinations thereof. The amino acid sequences of the VH CDR1s of DNV1, DNV2, DNV3, DNV4, DNV5, DNV6 and DNV7 are shown in SEQ ID NOs:32-38 respectively. The amino acid sequences of the VH CDR2s of DNV1, DNV2, DNV3, DNV4, DNV5, DNV6 or DNV7 are shown in SEQ ID NOs:39-45. The amino acid sequences of the VH CDR3s of DNV1, DNV2, DNV3, DNV4, DNV5, DNV6 and DNV7 are shown in SEQ ID NOs:46-52, respectively The amino acid sequences of the VL CDR1s of DNV1, DNV2, DNV3, DNV4, DNV5, DNV6 and DNV7 are shown in SEQ ID NOs:18-24, respectively. The amino acid sequences of the VL CDR2s of DNV1, DNV2, DNV3, DNV4, DNV5, DNV6 and DNV7 are DNN, AAS, DDD, WAS, AAS, GNT, AAS, respectively. The amino acid sequences of the VL CDR3s of DNV1, DNV2, DNV3, DNV4, DNV5, DNV6 or DNV7 are shown in SEQ ID NOs:25-31, respectively. The CDR regions are delineated using the Kabat system (Kabat et al. (1991) Sequences of Proteins of Immunological Interest, Fifth Edition, U.S. Department of Health and Human Services, NIH Publication No. 91-3242).

Given that each of these antibodies can bind to human LAG3 and that antigen-binding specificity is provided primarily by the CDR1, CDR2, and CDR3 regions, the VH CDR1, CDR2, and CDR3 sequences and VL CDR1, CDR2, and CDR3 sequences can be "mixed and matched" (i.e., CDRs from different antibodies can be mixed and match, although each antibody must contain a VH CDR1, CDR2, and CDR3 and a VL CDR1, CDR2, and CDR3) to create other anti-LAG3 binding molecules of the invention.

LAG3 binding of such "mixed and matched" antibodies can be tested using the binding assays described above and in the Examples (e.g., ELISAs, Biacore® analysis). Preferably, when VH CDR sequences are mixed and matched, the CDR1, CDR2 and/or CDR3 sequence from a particular VH sequence is replaced with a structurally similar CDR sequence(s). Likewise, when VL CDR sequences are mixed and matched, the CDR1, CDR2 and/or CDR3 sequence from a particular VL sequence preferably is replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences disclosed herein for monoclonal antibodies DNV1, DNV2, DNV3, DNV4, DNV5, DNV6 and DNV7.

Antibodies can be affinity matured by light-chain shuffling combined with or without random mutagenesis of its heavy chain variable domain and panning against LAGS. The VL CDR1, CDR2 and CDR3 of the antibodies mentioned in this invention can be optimized with light-chain shuffling to create other anti-LAG3 binding molecules of the invention.

Fab portion of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 are isolated and structurally characterized as described in Example 3. The VL amino acid sequences of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 are shown in SEQ ID NOs:81, 82, 83, 84, 85, 86, 87, 88, 89, 90, 91, 92, 93 and 94, respectively. The VH amino acid sequences of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 are shown in SEQ ID NO:3.

In another aspect, this disclosure provides antibodies that comprise the heavy chain and light chain CDR1s, CDR2s and CDR3s of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18. The amino acid sequences of the VL CDR1s of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 are shown in SEQ ID NOs:53, 54, 55, 56, 57, 58, 59, 60, 61, 62, 63, 64, 65, and 66 respectively. The amino acid sequences of the VL CDR2s of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 are SDN, GNS, YDD, SDD, SSN, YDD, YDT, YDD, GNS, SND, YDD, GDN, YDD and YDD respectively. The amino acid sequences of the VL CDR3s of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 shown in SEQ ID NOs: 67, 68, 69, 70, 71, 72, 73, 74, 75, 76, 77, 78, 79, 80, respectively.

The amino acid sequences of the VH CDR1s of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 are SEQ ID NO:34. The amino acid sequences of the VH CDR1s of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 are SEQ ID NO:41. The amino acid sequences of the VH CDR1s of DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 are SEQ ID NO:48.

An antibody of the invention further can be prepared using an antibody having one or more of the VH and/or VL sequences disclosed herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs.

Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) Nature 332:323-327; Jones et al. (1986) Nature 321: 522-525; Queen et al. (1989) Proc. Natl. Acad. See. U.S.A. 86: 10029-10033; U.S. Pat. Nos. 5,225, 539; 5,530,101; 5,585,089; 5,693,762 and 6,180,370.)

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence of SEQ ID NOs:34, SEQ ID NOs:41, and SEQ ID NOs:48, respectively, and a light chain variable region comprising CDR1 sequence selected from the group consisting of SEQ ID NOs:20, 53-66; CDR2 sequence selected from the group consisting of DDD, SDN, GNS, YDD, SDD, SSN, YDD, YDT, YDD, GNS, SND, YDD, GDN, YDD and YDD; and CDR3 sequence selected from a group consisting of SEQ ID NOs:27, 67-80. Thus, such antibodies contain the VH and VL CDR sequences of monoclonal antibodies DNV3, DNV3.1, DNV3.2, DNV3.3, DNV3.4, DNV3.5, DNV3.7, DNV3.8, DNV3.9, DNV3.12, DNV3.13, DNV3.14, DNV3.15, DNV3.16 and DNV3.18 can contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al. (1991), cited supra; Tomlinson et al. (1992) "The Repertoire of Human Germline V H Sequences Reveals about Fifty Groups of VH Segments with Different Hypervariable Loops" *J. Mol. Biol.* 227:776-798; and Cox et al. (1994) "A Directory of Human Germ-line V H Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the GenBank database. For example, the following heavy chain germline sequences found in the HCo7 HuMAb mouse are available in the accompanying GenBank Accession Nos.:1-69 (NG_0010109, NT_024637 & BC070333), 3-33 (NG_0010109 & NT_024637) and 3-7 (NG_0010109 &NT_024637). As another example, the following heavy chain germline sequences found in the HCo12 HuMAb mouse are available in the accompanying GenBank Accession Nos.: 1-69 (NG_0010109, NT_024637 & BC070333), 5-51 (NG_0010109 & NT_024637), 4-34 (NG_0010109 & NT_024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997), supra), which is well known to those skilled in the art. The compositions and methods of the present invention are not limited to variants of the exemplary sequences disclosed herein but include those having at least 90%, at least 95% and at least 99% identity to an exemplary sequence disclosed herein.

In preferred embodiments, an isolated monoclonal anti-LAG3 IgG4 antibody, or antigen-binding portion thereof, comprises: (a) a heavy chain comprising the amino acid sequence of SEQ ID NO:17 and (b) a light chain comprising the amino acid sequence of SEQ ID NO:107, SEQ ID NO:108 or SEQ ID NO:109; wherein the antibody binds human LAG3, inhibits binding of LAG3 to major histocompatibility (MHC) class II molecule and stimulates an immune response.

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug. The pharmaceutical compositions of the invention also can be administered in combination therapy with, for example, another immunostimulatory agent, anti-cancer agent, an antiviral agent, or a vaccine, such that the anti-LAG3 antibody enhances the immune response against the vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a nonparenteral route, such as a topical, epidermal or mucosal route of administration, e.g., intranasally, orally, vaginally, rectally, sublingually or topically.

The pharmaceutical compositions of the invention can include pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylene diamine, procaine and the like.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable earner.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-LAG3 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities. In a preferred embodiment, the bispecific molecule comprises a first binding specificity for LAG3 and a second binding specificity for a triggering molecule that recruits cytotoxic effector cells that can kill a LAG3 expressing target cell. Examples of suitable triggering molecules are CD64, CD89, CD 16, and CD3. See, e.g., Kufer et al., TRENDS in Biotechnology, 22 (5), 238-244 (2004).

In an embodiment, a bispecific molecule has, in addition to an anti-Fc binding specificity and an anti-LAG3 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CDS, CD28, CD4, CD40, or ICAM-1) or other immune cells, resulting in an increased immune response against the target cell.

Bispecific molecules can come in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFvs) linked by a peptide chain, a so-called Bs(scFv)2 construct. Intermediate-sized bispecific molecules include two different F(ab) fragments linked by a peptidyllinker. Bispecific molecules of these and other formats can be prepared by genetic engineering, somatic hybridization, or chemical methods. See, e.g., Kufer et al, cited supra; Cao and Suresh, Bioconjugate Chemistry, 9(6), 635-644 (1998); and van Spriel et al., Immunology Today, 21 (8), 391-397 (2000), and the references cited therein.

Immunoconjugates

Antibodies of the invention can be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyllinker such as Val-Cit, Ala-Val, Val-Ala-Val, Lys-Lys, Pro-Val-Gly-Val-Val (SEQ ID NO: 114), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059, 404; WO 08/083,312; and WO 08/103,693; U.S. Patent Publications 20060024317; 20060004081; and 20060247295; the disclosures of which are incorporated herein by reference.

Antibodies of the invention can be labeled with radioisotopes or fluorescent dyes to form an immunoconjugate as to detect LAG3 protein. Suitable radioisotopes including $^{68}$Ga, $^{18}$F, $^{64}$Cu, $^{89}$Zr, $^{99m}$Tc, $^{111}$In, $^{123}$I, $^{124}$I, $^{125}$I, $^{131}$I. Radiolabeling antibodies with these radioisotopes are well known in the art.

EXAMPLE

Example 1

Panning and Screening of a Phage-Display Naïve Human Fab Library for Identification of LAG3 Antibodies We have recently constructed a large (size, $10^{11}$) phage-display naïve human Fab library with peripheral blood B cells from about 30 healthy individuals according to the previously published protocols (de Haard et al., J Biol Chem 1999, 274: 18218-18230). This library was used for selection of antibodies against recombinant human LAG3 conjugated to magnetic beads (Dynabeads M-270 epoxy; DYNAL Inc.) as described previously (Zhu et al., J Virol 2006, 80:891-899) except that we used 5, 1 and 0.1 μg of antigen in the first, second and third round of panning, respectively. Clones that bound to the antigen were identified from the third round of biopanning by using monoclonal phage ELISA as described (Zhu et al., J Virol 2006, 80:891-899).

The hexahistidine-tagged antibodies were expressed in *E. coli* strain HB2151 and purified from the soluble fraction of periplasm by using the Ni-NTA resin. 7 monoclonal antibodies against human LAG3 were selected by panning a large phage-display library of naïve human antibodies in the format of antigen-binding fragment (Fab). Then ELISA was performed according to standard protocols. Briefly, recombinant human LAG3 (Sino Biological Inc.) was coated on Corning EIA/RIA high-binding 96-well plates (Corning Inc.) at 50 ng per well overnight at 4° C. and blocked with 3% nonfat milk in PBS (pH7.4). Fivefold serially diluted antibodies were added and incubated at room temperature for 2 h. The plates were washed with PBS containing 0.05% Tween 20. Bound antibodies were detected by HRP-conjugated anti-FLAG tag antibody (Sigma-Aldrich). The assay was developed at room temperature with TMB substrate (Sigma-Aldrich) and monitored at 450 nm with a microplate reader. The results showed that 4 (DNV1, DNV3, DNV5, DNV6) of 7 antibodies had high affinities with $EC_{50}$ of ≤10 nM (FIG. 1).

Flow Cytometry

Figure 2:
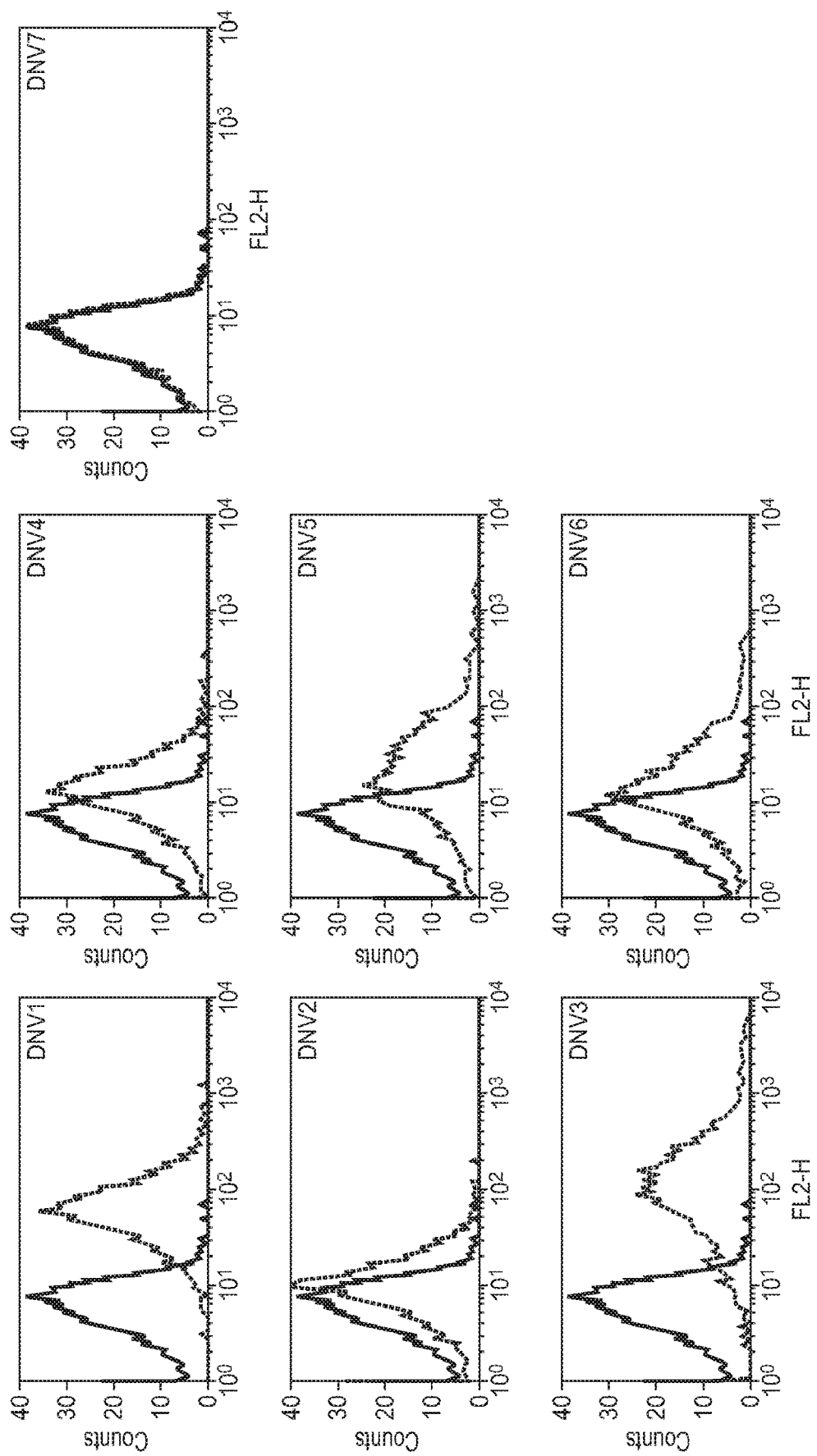
FIG. 2 illustrates binding of the antibodies in the format of Fab to cell surface LAG3 as measured by flow cytometry.

To measure the binding of Fab antibodies against LAG3, about $5 \times 10^5$ PHA-activated human PBMCs (LAG3 positive) were incubated with antibodies on ice for 30 min. The cells were washed once with PBS containing 0.1% bovine serum albumin (PBSA) and resuspended in 200 µl PBSA. Then 2 µl anti-His-PE conjugates (Miltenyi Biotec) were added and incubated for 30 min. The cells were washed once with PBSA and then used for flow cytometry analysis (FIG. 2).

Figure 3:
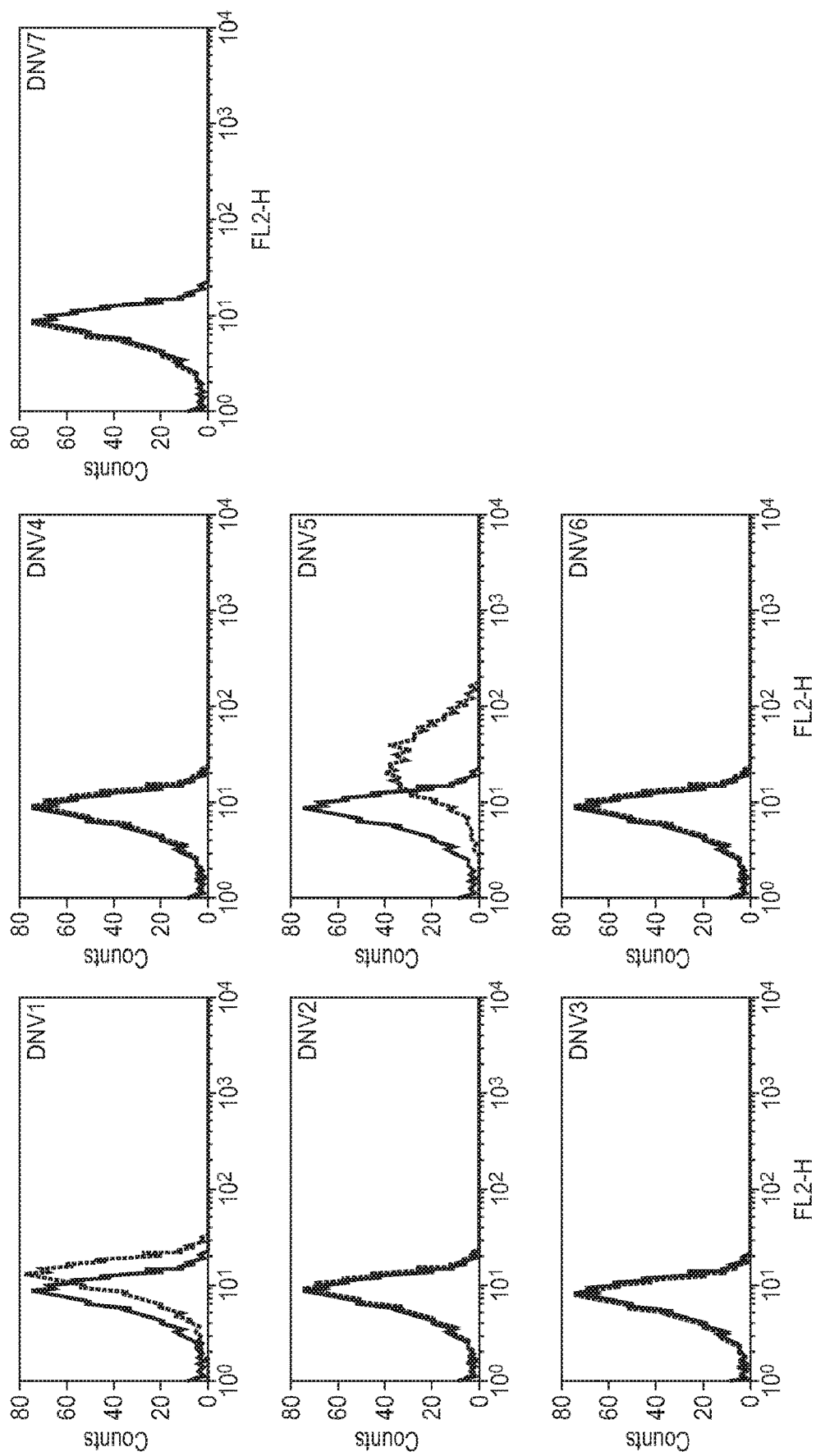
FIG. 3 illustrates binding of the antibodies in the format of Fab to LAG3-negative cells as measured by flow cytometry.

Binding of the antibodies in the format of Fab to LAG3-negative cells was also measured by flow cytometry. About $5 \times 10^5$ cells were incubated with 3 µg/ml antibodies on ice for 30 min. The cells were washed once with PBS containing 0.1% bovine serum albumin (PBSA) and resuspended in 200 µl PBSA. Then 2 µl anti-His-PE conjugates (Miltenyi Biotec) were added and incubated for 30 min. The cells were washed once with PBSA and then used for flow cytometry analysis. The results showed that DNV5 and DNV1 had some levels of nonspecific binding while others did not react with the LAG3-negative cells (FIG. 3).

Figure 4:
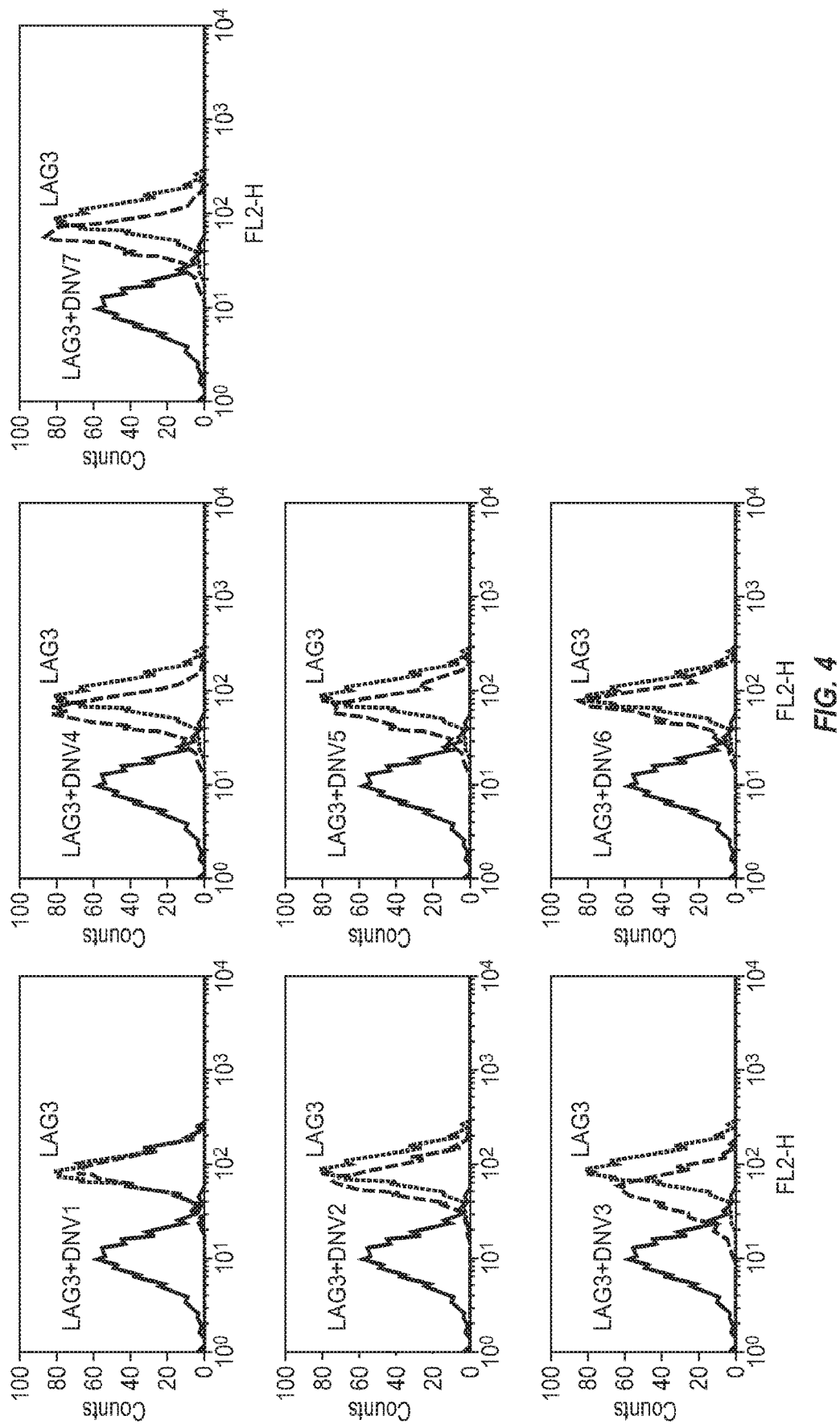
FIG. 4 illustrates inhibition of recombinant human LAG3 binding to MHC class II (MHCII)-expressing cells by the antibodies in the format of Fab as measured by flow cytometry. The curve on the left is the baseline. The curve on the right is for cells incubated with biotinylated human LAG3. The middle curve is for cells incubated with both biotinylated human LAG3 and antibodies. DNV3 had strong competition with LAG3 for binding to the cells while others had no or relatively weak competitive activity.

To test if the LAG3 antibodies could inhibit binding of LAG3 to its ligand MHCII on cell surface, about $5 \times 10^5$ cells were incubated with 2 µg/ml biotinylated recombinant human LAG3 in the absence or presence of the antibodies at 40 µg/ml in 200 µl PBSA on ice for 30 min. The cells were washed once with PBSA and resuspended in 200 µl PBSA. Then 2 µl streptavidin-PE conjugates (Invitrogen) were added and incubated for 30 min. The cells were washed once with PBSA and then used for flow cytometry analysis. DNV3 had the strongest competition with LAG3 for binding to the cells while others had no or weak competitive activity (FIG. 4). These results suggest that this panel of LAG3 antibodies could be potentially useful for clinical development to treat cancer.

Example 2. Methods of Making Anti-LAG3 Human Monoclonal Antibodies

Cloning of IgG1 and IgG4 of Anti-LAG3 Antibody DNV3

To clone the IgG1 of DNV3, we used the following primers:

```
bnIgG20L1,
                                   (SEQ ID NO: 95)
5'-GTGTAAGCTTACCATGGGTGTGCCCACTCA

GGTCCTGGGGTTGCTG-3';
(sense)

bnIgG20H1,
                                   (SEQ ID NO: 96)
5'-GTGTTCTAGAGCCGCCACCATGGAATGGAG

CTGGGTCTTTCTCTTC-3';
(sense)

8LF1,
                                   (SEQ ID NO: 97)
5'-GATGCCAGATGTCAGTCTGTGTTGACGCAG-3';
(sense)

8LR1,
                                   (SEQ ID NO: 98)
5'-GCCAGAGAATCGGTCAGGAATCCCTGAGGGTCGCTTATC-3';
(antisense)

8LF2,
                                   (SEQ ID NO: 99)
5'-CCTGACCGATTCTCTGGC-3';
(sense)

8LR2,
                                   (SEQ ID NO: 100)
5'-GATCGAATTCTTATGAACATTCTGTAGGGGC-3';
(antisense)

8HF,
                                   (SEQ ID NO: 101)
5'-GGTGTCCACTCCGAGGTCCAGCTGGTGCAG-3';
(sense)

8HR,
                                   (SEQ ID NO: 102)
5'-GAAGCTGAGCTCACGGTGACCATTGTCCC-3';
(antisense)

IgG4CF,
                                   (SEQ ID NO: 103)
5'-GATCGAGCTCAGCTTCCACCAAGGGCCCATCC-3';
(sense)

IgG4CR,
                                   (SEQ ID NO: 104)
5'-CGGCCGTCGCACTCATTTACCCAGAGACAGGGAGAG-3';
(antisense)

AAAF,
                                   (SEQ ID NO: 105)
5'-TGAGTGCGACGGCCGGCA-3';
(sense)

AAAR,
                                   (SEQ ID NO: 106)
5'-CCCGAGGTCGACGCTCTC-3'.
(antisense)
```

For cloning of DNV3 IgG1, the gene fragments encoding the N and C terminal portions of DNV3 light chain were PCR amplified with primer pairs 8LF1/8LR1 and 8LF2/8LR2, respectively. Full-length DNV3 light chain was assembled by overlapping PCR with the two gene fragments in the same molarities for 7 cycles in the absence of primers and 15 additional cycles in the presence of primers 8LF1 and 8LR2. The PCR product was linked to a gene fragment encoding a leader peptide by overlapping PCR with primers bnIgG20L1 and 8LR2. The final PCR product was digested with HindIII and EcoRI, and cloned into the pDin1 vector. For cloning of DNV3 heavy chain into the vector, the DNV3 VH gene fragment was PCR amplified with primers 8HF and 8HR. The PCR product was linked to a gene fragment encoding a leader peptide by overlapping PCR with primers bnIgG20H1 and 8HR. The product was digested with XbaI and SacI, and cloned into the pDin1 construct with DNV3 light chain.

For cloning of DNV3 IgG4, a gene fragment encoding the human IgG4 constant region and a polyA signal fragment were PCR amplified with primer pairs IgG4CF/IgG4CR and AAAF/AAAR, respectively. The products were joined together by overlapping PCR with primers IgG4CF and AAAR. The overlapping PCR product was digested with SacI and SalI, and cloned into the pDin1-based construct encoding DNV3 IgG1.

Protein Expression and Purification

IgG antibodies were expressed in 293FS cells as described previously (Chen et al., Proc Natl Acad Sci USA 2008, 105: 17121-17126). IgG antibodies were purified from the 293FS culture supernatant by using Protein A Sepharose 4 Fast Flow column chromatography (GE Healthcare) according to the manufacturer's instructions.

ELISA

Figure 5:
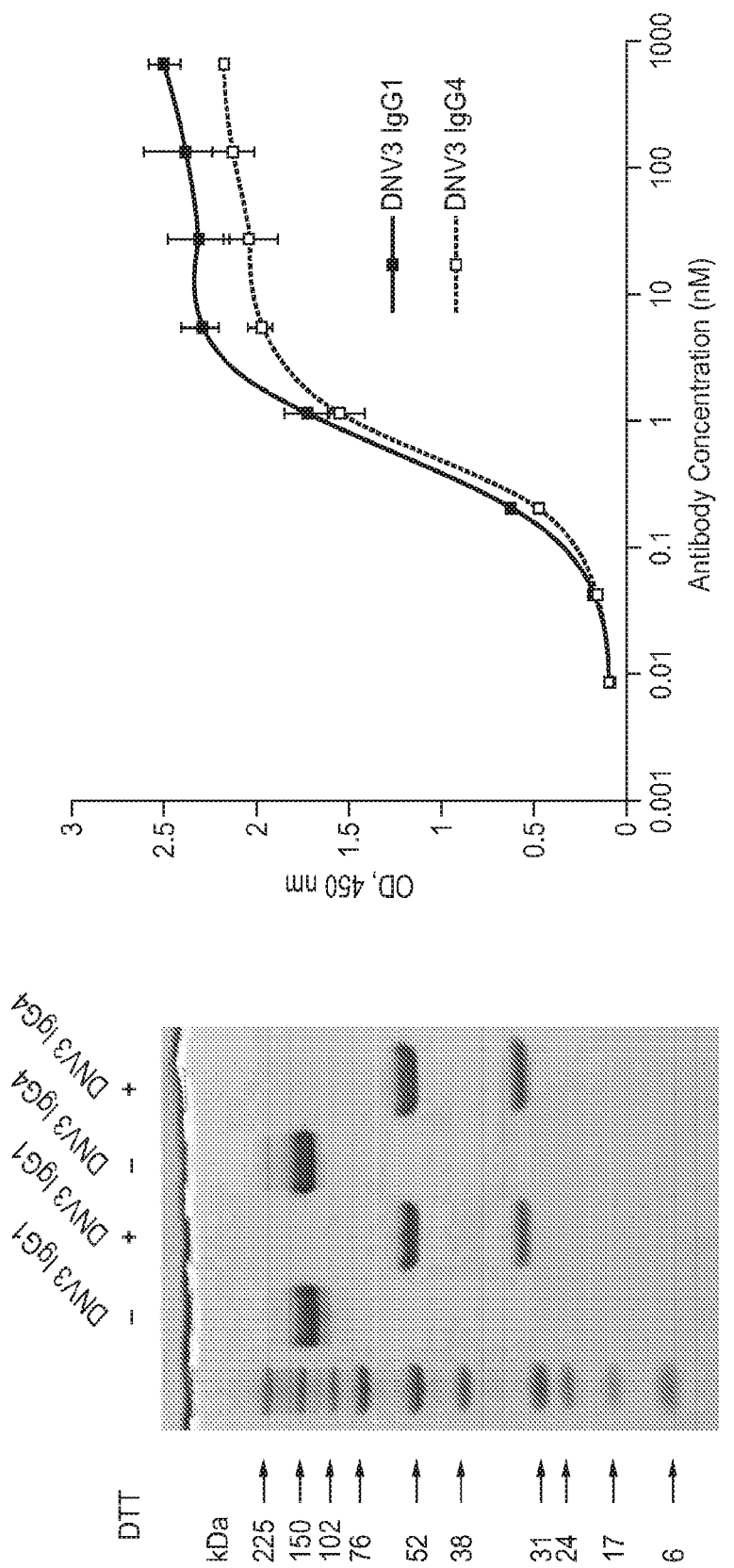
FIG. 5 illustrates generation and ELISA binding of DNV-3 IgG1 and IgG4 to recombinant human LAG3.
Figure 6:
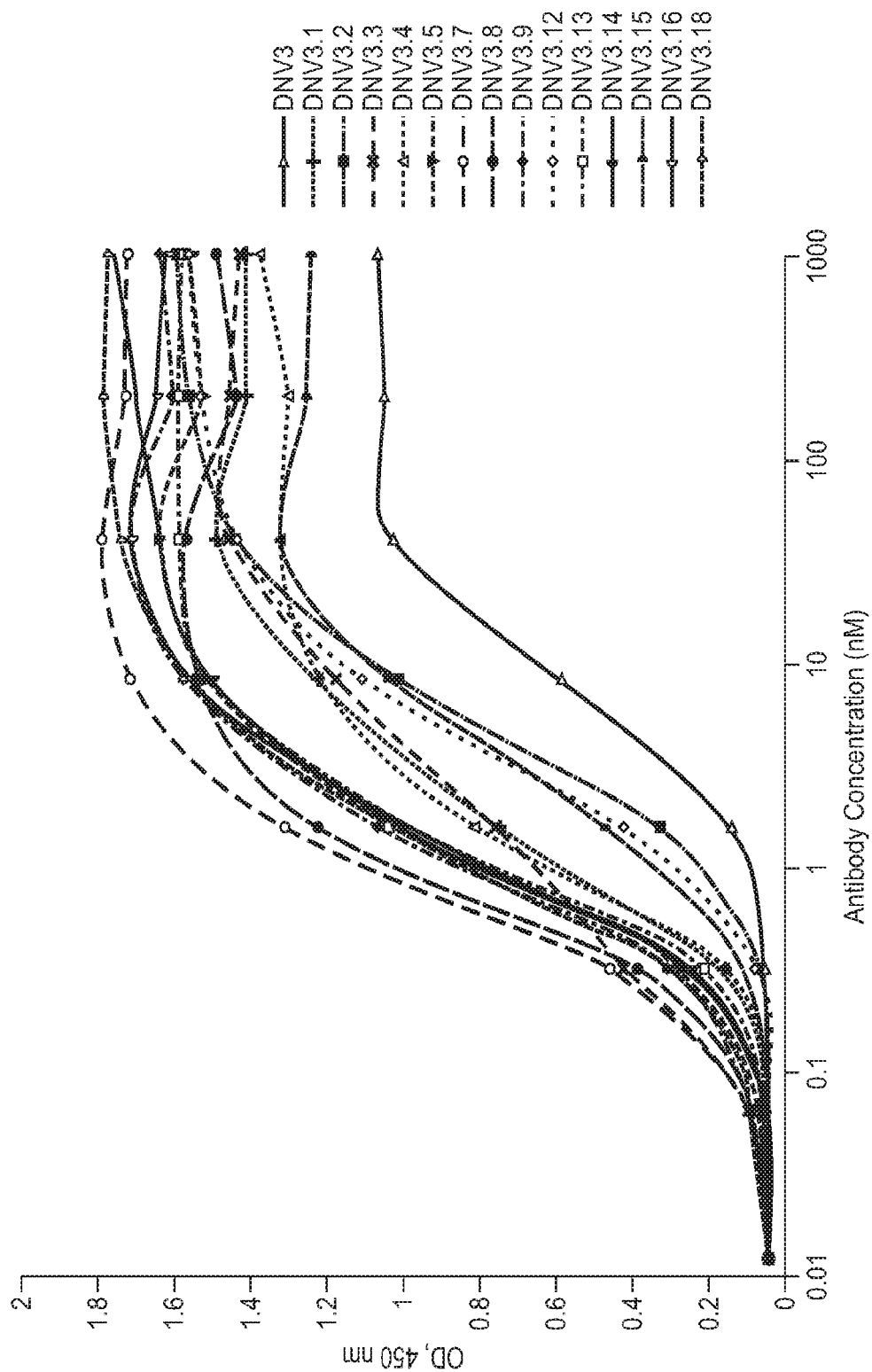
FIG. 6 illustrates ELISA test of affinity-matured DNV3 Fab variant by light chain shuffling.

ELISA was performed according to standard protocols. Briefly, recombinant human LAG3 (Sino Biological Inc.) was coated on Corning EIA/RIA high-binding 96-well plates (Corning Inc.) at 50 ng per well overnight at 4° C. and blocked with 3% nonfat milk in PBS (pH7.4). Fivefold serially diluted antibodies were added and incubated at room temperature for 2 h. The plates were washed with PBS containing 0.05% Tween 20. Bound Fab and IgG antibodies were detected by HRP-conjugated anti-FLAG tag antibody and HRP-conjugated anti-human IgG (Fc-specific) antibody (Sigma-Aldrich), respectively. The assay was developed at room temperature with TMB substrate (Sigma-Aldrich) and monitored at 450 nm with a microplate reader. The half-maximal binding ($EC_{50}$) was calculated by fitting the data to the Langmuir adsorption isotherm. DNV3 IgG1 and IgG4 were cloned into the plasmid vectors pDin1 and pDin4, respectively. They were expressed and purified from transiently transfected 293 freestyle cell cultures with a yield of approximately 15 mg/ml. In ELISA, both DNV3 IgG1 and IgG4 bound to recombinant human LAG3 with an $EC_{50}$ of approximately 0.5 nM (FIG. 5).

Example 3. Light Chain Shuffling of DNV3 Fab

Figure 7:
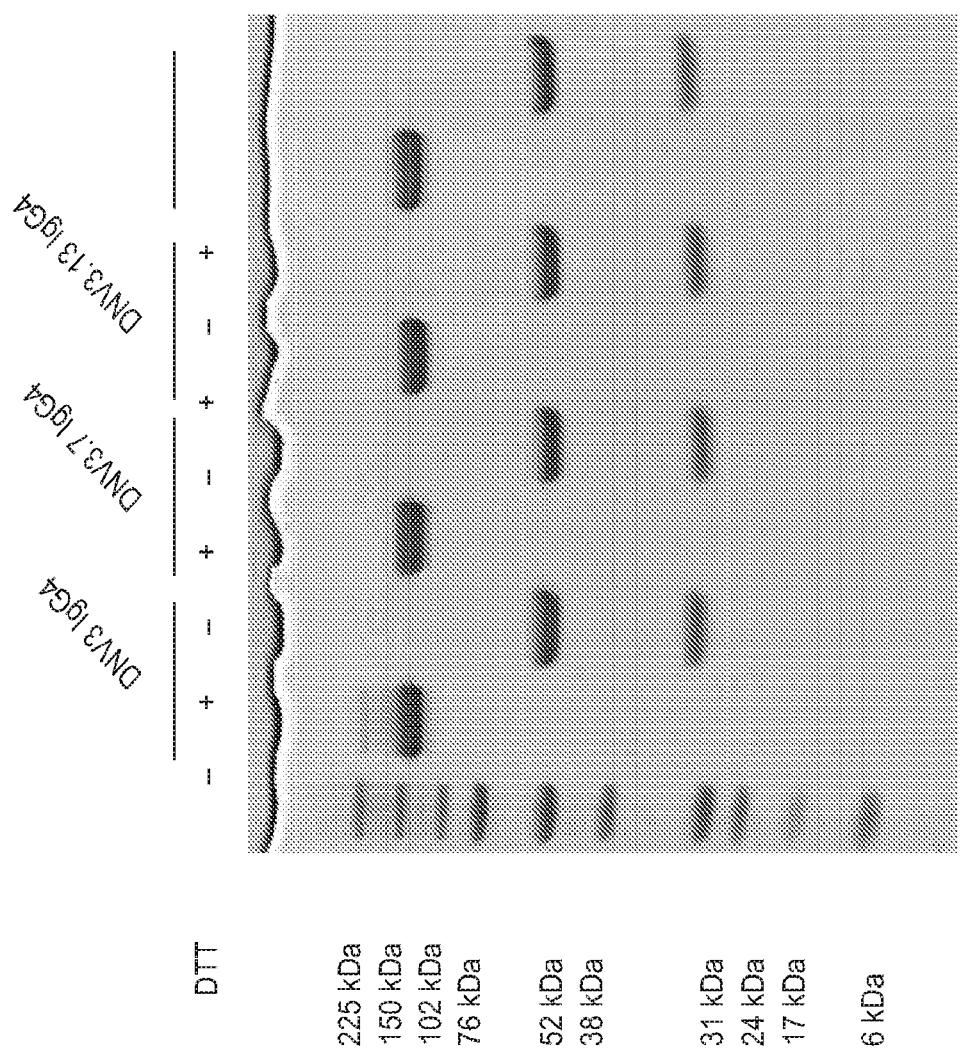
FIG. 7 illustrates the SDS-PAGE analysis of affinity-matured DNV3 IgG4 variants.

Affinity maturation of DNV3 was conducted according to the previously reported protocol (Zhu et al., J Infect Dis 2008, 197: 846-853). Briefly, a phage-display light-chain shuffling Fab library was constructed, panned and screened for DNV3 variants with higher binding to recombinant human LAG3. A total of 14 DNV3 variants were identified which had the same heavy chain as DNV3 but different light chains. ELISA was performed to measure the binding activity of the selected DNV3 variants. Briefly, recombinant human LAG3 (Sino Biological Inc.) was coated on Corning EIA/RIA high-binding 96-well plates (Corning Inc.) at 50 ng per well overnight at 4° C. and blocked with 3% nonfat milk in PBS (pH7.4). Fivefold serially diluted antibodies were added and incubated at room temperature for 2 h. The plates were washed with PBS containing 0.05% Tween 20. Bound antibodies were detected by HRP-conjugated anti-FLAG tag antibody (Sigma-Aldrich). The assay was developed at room temperature with TMB substrate (Sigma-Aldrich) and monitored at 450 nm with a microplate reader. The result showed that all purified DNV3 variants had higher binding ($EC_{50}$s, 0.6-4 nM) than DNV3 ($EC_{50}$, 6 nM) (FIG. 6).

Example 4. IgG4 Antibodies of Affinity-Matured DNV3 Variants

Cloning of IgG4 of Affinity-Matured DNV3 Variants

We used the following primers:

```
8HF,
                                   (SEQ ID NO: 101)
5'-GGTGTCCACTCCGAGGTCCAGCTGGTGCAG-3';
(sense)

8HR,
                                   (SEQ ID NO: 102)
5'-GAAGCTGAGCTCACGGTGACCATTGTCCC-3';
(antisense)

8LF1,
```

-continued

```
                                   (SEQ ID NO: 97)
5'-GATGCCAGATGTCAGTCTGTGTTGACGCAG-3';
(sense)

8LR1,
                                   (SEQ ID NO: 98)
5'-GCCAGAGAATCGGTCAGGAATCCCTGAGGGTCGCTTATC-3';
(antisense)

8LF2,
                                   (SEQ ID NO: 99)
5'-CCTGACCGATTCTCTGGC-3';
(sense)

8LR2,
                                   (SEQ ID NO: 100)
5'-GATCGAATTCTTATGAACATTCTGTAGGGGC-3';
(antisense)

8.7F,
                                   (SEQ ID NO: 110)
5'-GATGCCAGATGTTCCTATGAGCTGACTCAG-3';
(sense)

8.7R,
                                   (SEQ ID NO: 111)
5'-GATCGAATTCTTATGAACATTCTGTAGGGGC-3';
(antisense)

8.13F:
                                   (SEQ ID NO: 112)
5'-GATGCCAGATGTTCCTATGTGCTGACTCAG-3';
(sense)

8.18F,
                                   (SEQ ID NO: 113)
5'-GATGCCAGATGTTCTGTCGTGACGCAGCCG-3';
(sense)

bnIgG20L1,
                                   (SEQ ID NO: 95)
5'-GTGTAAGCTTACCATGGGTGTGCCCACTCAGG

TCCTGGGGTTGCTG-3';
(sense)

bnIgG20H1,
                                   (SEQ ID NO: 96)
5'-GTGTTCTAGAGCCGCCACCATGGAATGGAGCT

GGGTCTTTCTCTTC-3';
(sense)
```

For cloning of DNV3 IgG4, the DNV3 VH gene fragment was PCR amplified with primers 8HF and 8HR. The PCR product was linked to a gene fragment encoding a leader peptide by overlapping PCR with primers bnIgG20H1 and 8HR. The product was digested with XbaI and SacI, and cloned into the pDin4 construct. For cloning of DNV3 light chain into the vector, two gene fragments encoding the N and C terminus of DNV3 light chain were PCR amplified with primer pairs 8LF1/8LR1 and 8LF2/8LR2, respectively. The two fragments were joined to each other by overlapping PCR with primers 8LF1 and 8LR2. The overlapping PCR product was further linked to a gene fragment encoding a leader peptide by overlapping PCR with primers bnIgG20L1 and 8LR2. The final PCR product was digested with HindIII and EcoRI, and cloned into the pDin4 vector containing DNV3 VH. The IgG4s of DNV3.7, DNV3.13 and DNV3.18 were cloned the same way except for the use of primer pairs 8.7F/8.7R, 8.13F/8.7R and 8.18F/8.7R for amplification of light chains, respectively.

Protein Expression and Purification:

The IgG4s of DNV3 variants were expressed in 293FS cells as described previously (Chen et al., Proc Natl Acad Sci USA 2008, 105: 17121-17126) and purified from the 293FS culture supernatant by using Protein A Sepharose 4 Fast Flow column chromatography (GE Healthcare) according to the manufacturer's instructions. The IgG4s of DNV3 variants were cloned into the plasmid vector pDin4. They were expressed and purified from transiently transfected 293 freestyle cell cultures with a yield of approximately 15 mg/ml. Purified DNV3 IgG4 variants were analysis by SDS-PAGE (FIG. 7).

Figure 9:
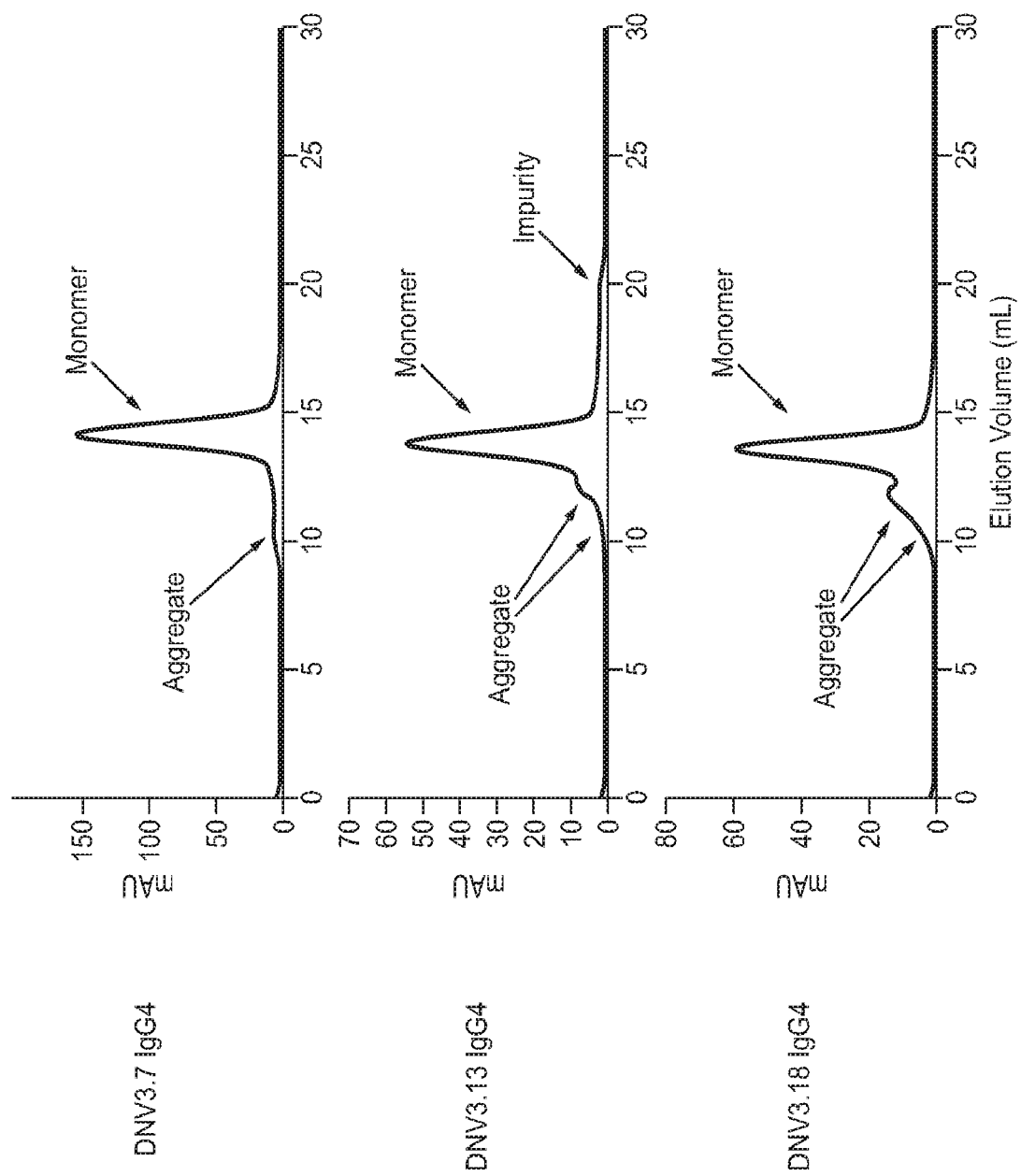
FIG. 9 illustrates size-exclusion chromatography of affinity matured DNV3 IgG4 variants produced from 293 Freestyle cells.
Figure 10:
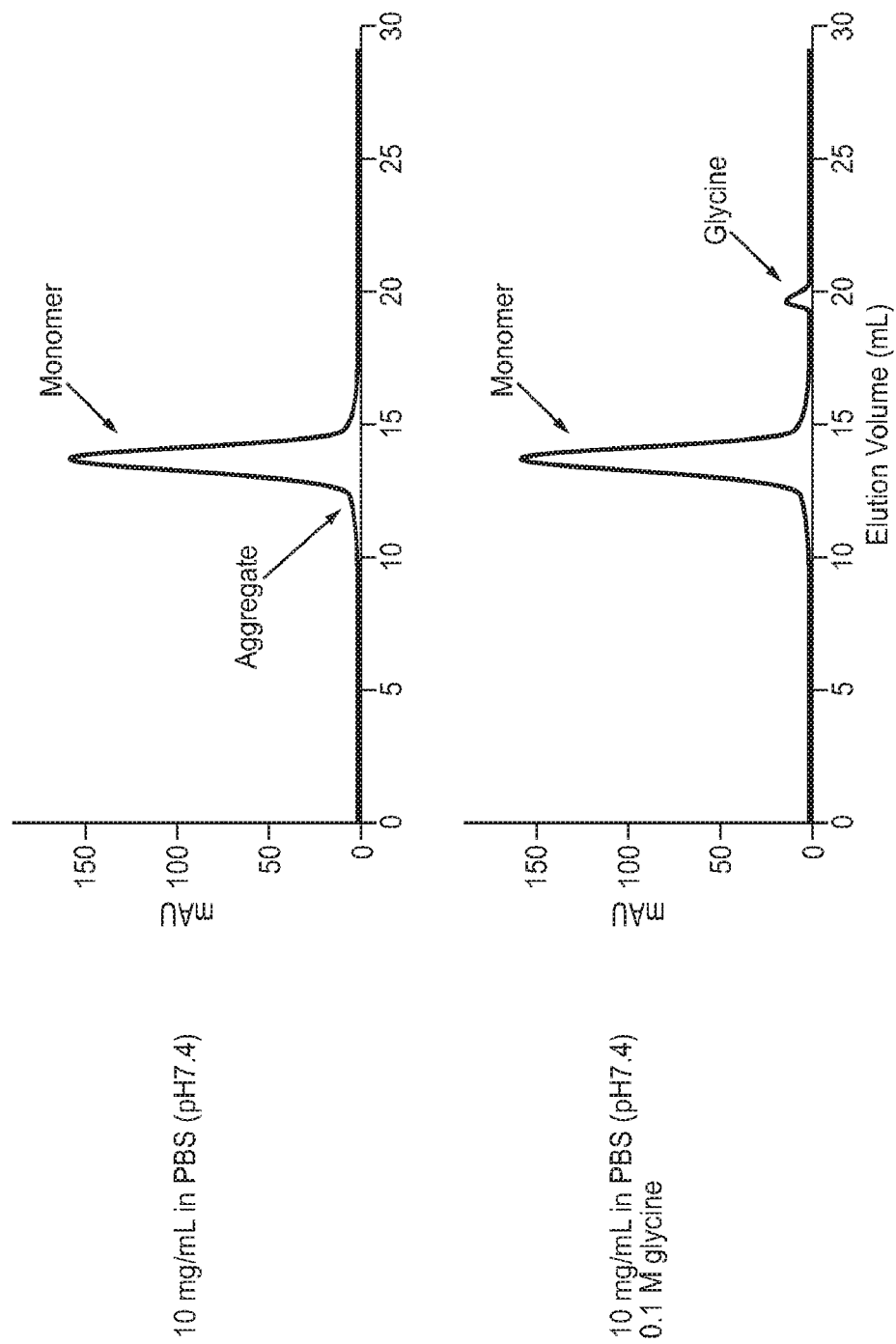
FIG. 10 illustrates size-exclusion chromatography of DNV3.7 IgG4 produced from CHO stable cell lines.

Size-Exclusion Chromatography:

A Superdex200 10/300 GL column (GE Healthcare) was calibrated with protein molecular mass standards of carbonic anhydrase (29 kDa), ovalbumin (44 kDa), conalbumin (75 kDa), aldolase (158 kDa) and ferritin (440 kDa). Purified proteins at a concentration of 1 mg mL-1 or 10 mg mL-1 in PBS with or without 0.1 M glycine (pH7.4) were loaded onto the pre-equilibrated column and eluted with PBS (pH7.4) at 0.5 mL/min. SEC revealed that the vast majority (>95%) of the purified DNV3.7 IgG4 in PBS (pH7.4) is a monomer while the DNV3.13 and DNV3.18 IgG4 proteins contain a relatively large amount of aggregates (FIG. 9). SEC revealed that the vast majority (>95%) of the purified DNV3.7 IgG4 at a concentration of 10 mg/ml in PBS (pH7.4) is a monomer. An addition of 0.1 M glycine to the PBS buffer further reduces aggregates to an undetectable level (FIG. 10).

ELISA Binding of DNV3.7 IgG4 to Recombinant LAG3 from Different Species.

Figure 11:
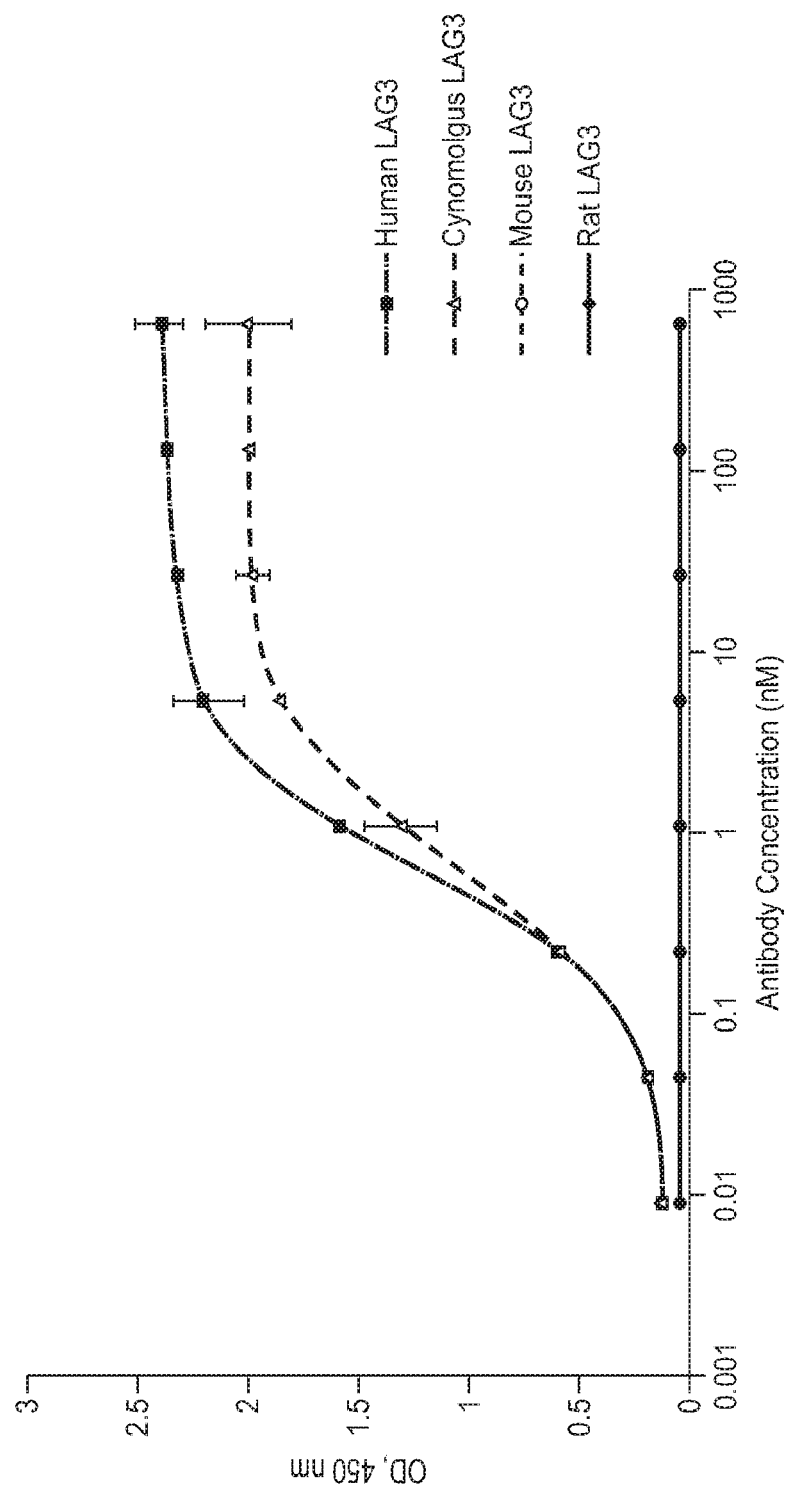
FIG. 11 illustrates ELISA binding of DNV3.7 IgG4 to LAG3 from different species.

ELISA was performed according to standard protocols. Briefly, recombinant human, cynomolgus, mouse and rat LAG3 (Sino Biological Inc.) were coated on Corning EIA/RIA high-binding 96-well plates (Corning Inc.) at 50 ng per well overnight at 4° C. and blocked with 3% nonfat milk in PBS (pH7.4). Fivefold serially diluted IgG4 antibodies were added and incubated at room temperature for 2 h. The plates were washed with PBS containing 0.05% Tween 20. Bound IgG4s were detected by HRP-conjugated anti-human IgG (Fc-specific) antibody (Sigma-Aldrich). The assay was developed at room temperature with TMB substrate (Sigma-Aldrich) and monitored at 450 nm with a microplate reader. The half-maximal binding (EC50) was calculated by fitting the data to the Langmuir adsorption isotherm. The results showed that DNV3 IgG4 strongly bound to human and cynomolgus LAG3 but not to mouse and rat LAG3 (FIG. 11).

Figure 8:
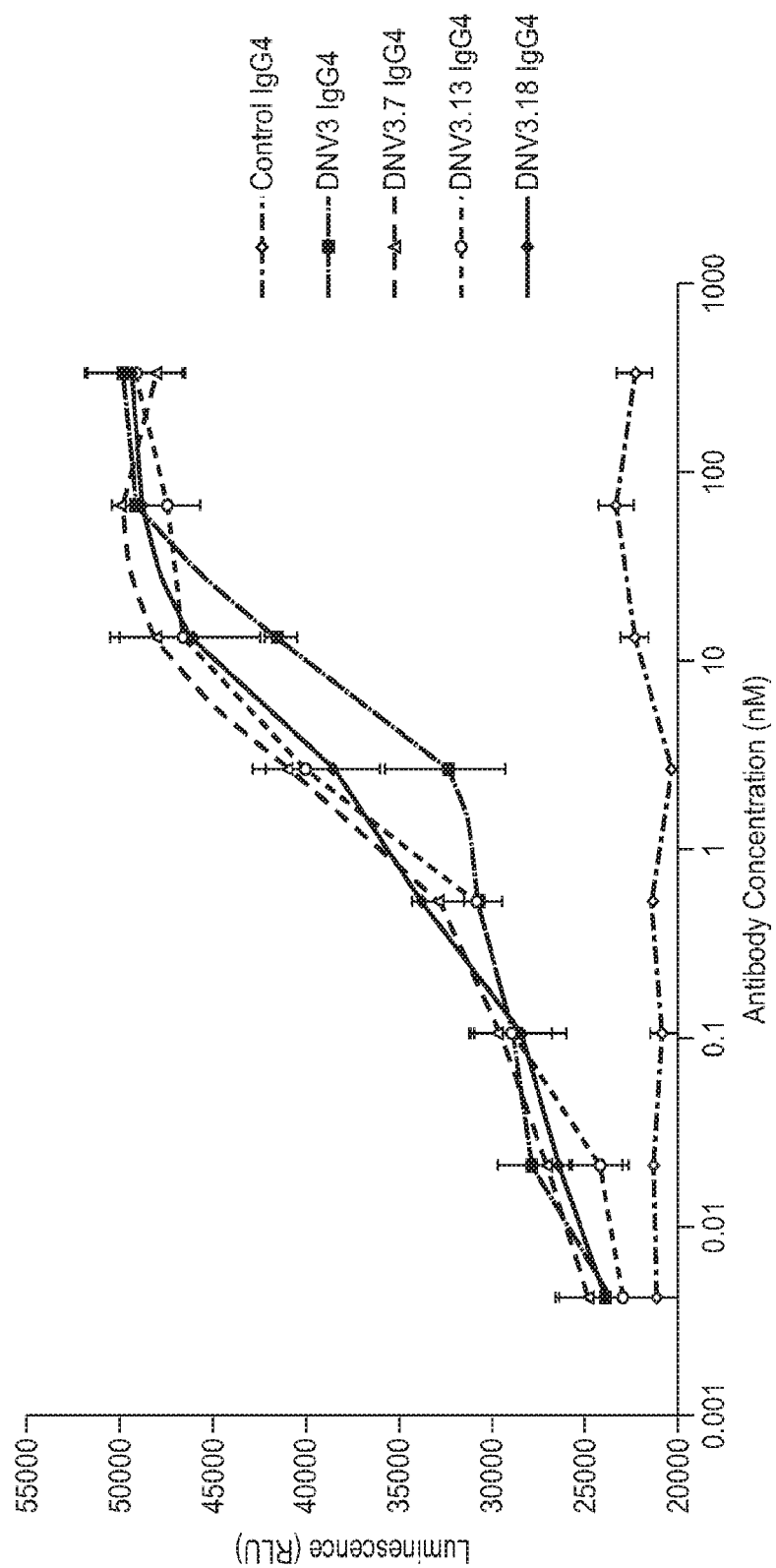
FIG. 8 illustrates T cell activation assay of IgG4 variants. Affinity matured DNV3 IgG4 variants effectively activate T cells in a Promega LAG3-MHC II Bioassay.

T Cell Activation Assay:

T cell activation assay was performed by using Promega LAG3-MHCII Blockade Bioassay Kit (Cat. No.: CS194802) according to the manufacturer's instructions. The results showed that the IgG4s of affinity matured DNV3 variants (EC50s, 1-2 nM) were more capable of activating T cells than the original DNV3 IgG4 (EC50, 8.7 nM). (FIG. 8)

Figure 12:
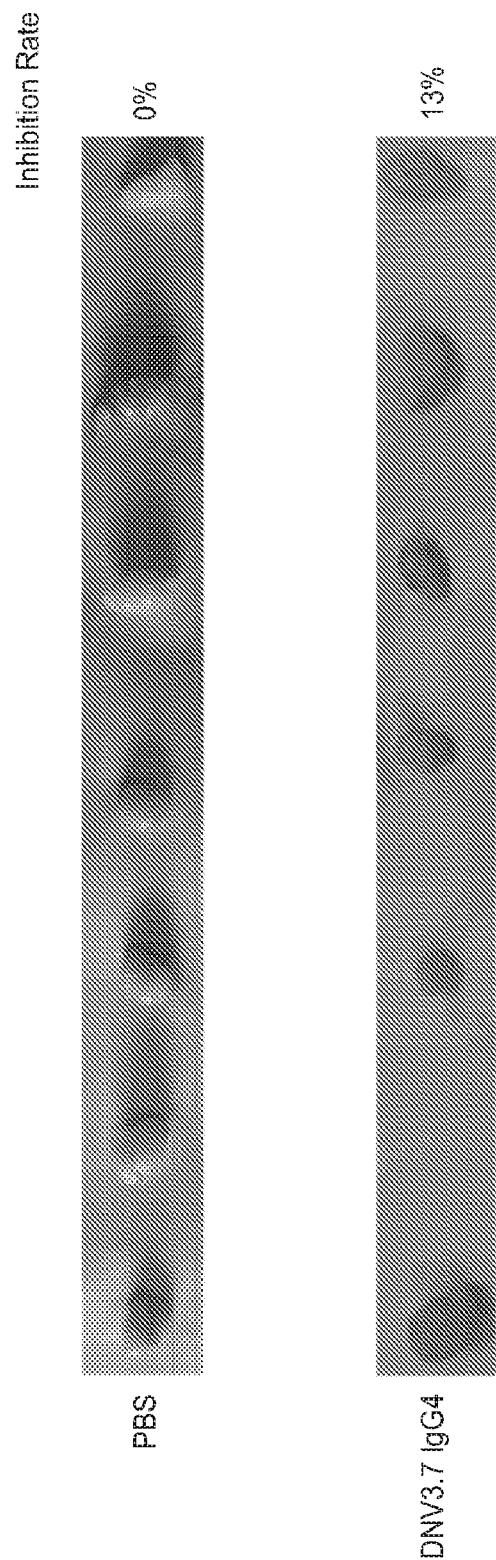
FIG. 12 illustrates the anti-tumor activity of DNV3.7 IgG4 in a mouse xenograft model of human gastric cancer cell line NCI-N87.

In-Vivo Tumor Growth Inhibition:

SCID mice were inoculated with $10^7$ NCI-N87 cells subcutaneously into the left flank of the mice. Once tumors reached a volume of 100-150 mm$^3$, mice were randomized into groups of 7 mice/group of equal average tumor volume and reconstituted intravenously with $10^7$ human PBMCs. After one day, the mice were dosed intravenously with PBS (control) or 0.5 mg DNV3.7 IgG4 every 3-4 days for 6 doses. After one month of treatment, mice were sacrificed and tumor weights were measured. Tumor growth inhibition rates were calculated by using the following formula: average weight of PBS group–the average weight of antibody treated group/average weight of PBS group. The tumor growth inhibition rate is 13% for the group treated with DNV3.7 IgG4 (FIG. 12). The result suggests intravenous administration of DNV3.7 IgG4 can inhibit the growth of the cancer cells.

The disclosures of all publications, patents, patent applications and published patent applications referred to herein by an identifying citation are hereby incorporated herein by reference in their entirety. Websites references using "World-Wide-Web" at the beginning of the Uniform Resource Locator (URL) can be accessed by replacing "World-Wide-Web" with www.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. An isolated human monoclonal antibody, which binds to human LAG3, or antigen-binding portion thereof, comprising
   (a) a heavy chain variable region CDR1 comprising SEQ ID NO:34;
   (b) a heavy chain variable region CDR2 comprising SEQ ID NO:41;
   (c) a heavy chain variable region CDR3 comprising SEQ ID NO:48;
   (d) a light chain variable region CDR1 comprising SEQ ID NO:20;
   (e) a light chain variable region CDR2 comprising DDD; and
   (f) a light chain variable region CDR3 comprising SEQ ID NO:27.

2. The antibody, or antigen-binding portion thereof, of claim 1, which comprises: a heavy chain variable region comprising the amino acid sequence of SEQ ID NO:11 and a light chain variable region comprising the amino acid sequence of SEQ ID NO:3.

3. The antibody, or antigen-binding portion thereof, of claim 1, wherein the antibody is a IgG1 antibody comprising:
   (a) a heavy chain comprising the amino acid sequence of SEQ ID NO:16 and (b) a light chain comprising the amino acid sequence of SEQ ID NO:8; wherein the antibody binds human LAG3, inhibits binding of LAG3 to major histocompatibility (MHC) class II molecule and stimulates an immune response.

4. The antibody, or antigen-binding portion thereof, of claim 1, wherein the antibody is an IgG4 antibody comprising:
   (a) a heavy chain comprising the amino acid sequence of SEQ ID NO:17 and (b) a light chain comprising the amino acid sequence of SEQ ID NO:8; wherein the antibody binds human LAG3, inhibits binding of LAG3 to major histocompatibility (MHC) class II molecule and stimulates an immune response.

5. An isolated monoclonal antibody, which binds to human LAG3, or antigen-binding portion thereof, comprising:
   (a) a heavy chain variable region comprising an amino acid sequence comprising SEQ ID NO: 11; and
   (b) a light chain variable region comprising an amino acid sequence selected from the group consisting of SEQ ID NOs:81-93 and 94.

6. The antibody, or antigen-binding portion thereof, of claim 5, which binds to human LAG3 with an $EC_{50}$ of $1 \times 10^{-8}$ M or less.

7. The antibody, or antigen-binding portion thereof, of claim 5, which binds to human LAG3 with an $EC_{50}$ of $1 \times 10^{-9}$ M or less.

8. A composition comprising the antibody, or antigen-binding portion thereof, of claim 5, and a pharmaceutically acceptable carrier.

9. An immunoconjugate comprising the antibody, or antigen-binding portion thereof, of claim 5, linked to a therapeutic agent.

10. A monomeric Fc antibody comprising the antigen-binding portion of an antibody of claim 5.

11. A bispecific antibody comprising the antigen-binding portion of antibodies of claim 5.

12. A trispecific antibody comprising the antigen-binding portion of antibodies of claim 5.

13. A method of stimulating an antigen-specific T cell response comprising contacting said T cell with the antibody of claim 5 such that an antigen-specific T cell response is stimulated.

14. A method of stimulating an immune response in a subject comprising administering the antibody of claim 5 to the subject such that an immune response in the subject is stimulated.

15. A method for inhibiting the growth of tumor cells in a subject comprising administering to the subject the antibody of claim 5 such that growth of the tumor is inhibited in the subject.

16. A method of stimulating an immune response in a subject comprising administering to the subject the antibody of claim 5 and at least one additional immunostimulatory antibody such that an immune response in the subject is stimulated.

17. An isolated nucleic acid molecule encoding the antibody, or antigen-binding portion thereof, of claim 5.

18. An expression vector comprising the nucleic acid molecule of claim 17.

19. A host cell comprising the expression vector of claim 18.

20. A method for preparing an anti-LAG5 antibody which comprises expressing the antibody in the host cell of claim 19 and isolating the antibody from the host cell.

21. An isolated human monoclonal antibody, which binds to human LAG5, or antigen-binding portion thereof, comprising a heavy chain variable region (VH) comprising CDR1 comprising SEQ ID NO:34;
   CDR2 comprising SEQ ID NO:41; and
   CDR3 comprising SEQ ID NO:48;
   and a light chain variable region (VL) selected from (A)-(N):
   (A) a VL comprising
   CDR1 comprising SEQ ID NO:53;
   CDR2 comprising SDN; and
   CDR3 comprising SEQ ID NO:67;
   (B) a VL comprising
   CDR1 comprising SEQ ID NO:54;
   CDR2 comprising GNS; and
   CDR3 comprising SEQ ID NO:68;
   (C) a VL comprising
   CDR1 comprising SEQ ID NO:55;
   CDR2 comprising YDD; and
   CDR3 comprising SEQ ID NO:69;
   (D) a VL comprising
   CDR1 comprising SEQ ID NO:56;
   CDR2 comprising SDD; and
   CDR3 comprising SEQ ID NO:70;
   (E) a VL comprising
   CDR1 comprising SEQ ID NO:57;
   CDR2 comprising SSN; and CDR3 comprising SEQ ID NO:71;
(F) a VL comprising
CDR1 comprising SEQ ID NO:58;
CDR2 comprising YDD; and
CDR3 comprising SEQ ID NO:72;
(G) a VL comprising
CDR1 comprising SEQ ID NO:59;
CDR2 comprising YDT; and
CDR3 comprising SEQ ID NO:73;
(H) a VL comprising
CDR1 comprising SEQ ID NO:60;
CDR2 comprising YDD; and
CDR3 comprising SEQ ID NO:74;
(I) a VL comprising
CDR1 comprising SEQ ID NO:61;
CDR2 comprising GNS; and
CDR3 comprising SEQ ID NO:75;
(J) a VL comprising
CDR1 comprising SEQ ID NO:62;
CDR2 comprising SND; and
CDR3 comprising SEQ ID NO:76;
(K) a VL comprising
CDR1 comprising SEQ ID NO:63;
CDR2 comprising YDD; and
CDR3 comprising SEQ ID NO:77;
(L) a VL comprising
CDR1 comprising SEQ ID NO:64;
CDR2 comprising GDN; and
CDR3 comprising SEQ ID NO:78;
(M) a VL comprising
CDR1 comprising SEQ ID NO:65;
CDR2 comprising YDD; and
CDR3 comprising SEQ ID NO:79; and
(N) a VL comprising
CDR1 comprising SEQ ID NO:66;
CDR2 comprising YDD; and
CDR3 comprising SEQ ID NO:80.

* * * * *